US010369376B2

(12) United States Patent
Palaniswamy et al.

(10) Patent No.: US 10,369,376 B2
(45) Date of Patent: Aug. 6, 2019

(54) PHOTOTHERAPY APPARATUSES AND METHODS

(71) Applicant: NeoLight LLC, Scottsdale, AZ (US)

(72) Inventors: Sivakumar Palaniswamy, Tempe, AZ (US); Deepakshyam Krishnaraju, Tempe, AZ (US)

(73) Assignee: Neolight LLC, Scottsdale, AZ (US)

( * ) Notice: Subject to any disclaimer, the term of this patent is extended or adjusted under 35 U.S.C. 154(b) by 309 days.

(21) Appl. No.: 15/143,277

(22) Filed: Apr. 29, 2016

(65) Prior Publication Data
US 2017/0312542 A1    Nov. 2, 2017

(51) Int. Cl.
*A61N 5/06* (2006.01)
*A61F 7/00* (2006.01)
*A61F 7/08* (2006.01)

(52) U.S. Cl.
CPC ............ *A61N 5/0621* (2013.01); *A61F 7/007* (2013.01); *A61F 7/08* (2013.01); *A61F 2007/0071* (2013.01); *A61N 2005/0638* (2013.01); *A61N 2005/0661* (2013.01); *A61N 2005/0662* (2013.01)

(58) Field of Classification Search
CPC ................ A61N 5/0613; A61N 5/0614; A61N 2005/0615; A61N 5/0616; A61N 5/0618; A61N 5/0621; A61N 5/0622; A61N 5/0624; A61N 5/0625; A61N 25/063; A61N 2005/0632; A61N 2005/0635; A61N 2005/0636; A61N 2005/0637; A61N 2005/0638; A61N 2005/0658; A61N 2005/0661; A61N 2005/0622
USPC ................................ 607/88–91, 93; 128/898
See application file for complete search history.

(56) References Cited

U.S. PATENT DOCUMENTS

| | | | |
|---|---|---|---|
| 3,514,581 A | 5/1970 | Rocholl et al. | |
| 4,663,789 A | 5/1987 | Smith | |
| 4,798,936 A | 1/1989 | Johnson, Sr. | |
| 5,005,108 A * | 4/1991 | Pristash | G02B 6/0005 362/23.15 |
| 5,645,578 A * | 7/1997 | Daffer | A61H 23/00 600/21 |
| 5,766,233 A * | 6/1998 | Thiberg | A61N 5/06 607/88 |
| 5,792,214 A * | 8/1998 | Larsson | A61N 5/0621 362/130 |
| 5,926,293 A | 7/1999 | Ralli | |
| 6,290,713 B1 * | 9/2001 | Russell | A61N 5/0616 607/88 |
| 6,596,016 B1 | 7/2003 | Vreman et al. | |

(Continued)

FOREIGN PATENT DOCUMENTS

WO    2011153599    12/2011

OTHER PUBLICATIONS

Berk, et al., Comparison of Sandblasting, Laser Irradiation, and Conventional Acid Etching for Orthodontic Bonding of Molar Tubes, European Journal of Orthodontics, 2008, 30:183-189.
Bouzid, et al., Effect of Impact Angle on Glass Surfaces Eroded by Sand Blasting, Journal of the European Ceramic Society, 2000, 20:481-488.

(Continued)

*Primary Examiner* — Ahmed M Farah
(74) *Attorney, Agent, or Firm* — Quarles & Brady LLP

(57) ABSTRACT

A phototherapy treatment apparatus and methods are provided. In particular, the present disclosure provides a phototherapy treatment apparatus configured to diffusely transmit light emitted from a light source to a patient.

10 Claims, 24 Drawing Sheets

(56) References Cited

U.S. PATENT DOCUMENTS

| | | | | |
|---|---|---|---|---|
| 6,623,511 | B1* | 9/2003 | Daffer | A61F 7/0053 |
| | | | | 128/898 |
| 6,669,627 | B1* | 12/2003 | Campbell | A61N 5/0618 |
| | | | | 600/27 |
| 6,712,481 | B2 | 3/2004 | Parker et al. | |
| 7,052,167 | B2* | 5/2006 | Vanderschuit | A61F 7/02 |
| | | | | 362/231 |
| 7,305,163 | B2 | 12/2007 | Williams | |
| 7,947,033 | B2* | 5/2011 | Ganapathy | A61B 5/0059 |
| | | | | 604/543 |
| 9,913,994 | B2* | 3/2018 | Marchese | A61N 5/0616 |
| 10,166,402 | B2 | 1/2019 | Brennan et al. | |
| 2007/0021807 | A1* | 1/2007 | Kurtz | A61N 5/0616 |
| | | | | 607/88 |
| 2007/0100400 | A1* | 5/2007 | Chung | A61N 5/0621 |
| | | | | 607/88 |
| 2007/0239232 | A1* | 10/2007 | Kurtz | A61N 5/0613 |
| | | | | 607/87 |
| 2009/0067178 | A1* | 3/2009 | Huang | G02B 5/0242 |
| | | | | 362/326 |
| 2010/0149809 | A1 | 6/2010 | Ruud et al. | |
| 2015/0289817 | A1 | 10/2015 | Augustine et al. | |
| 2015/0373781 | A1* | 12/2015 | Augustine | H05B 1/0272 |
| | | | | 219/212 |

OTHER PUBLICATIONS

Ennever, et al., Phototherapy for Neonatal Jaundice: Optimal Wavelengths of Light, Journal of Pediatrics, 1983, 103(2):295-299.

Evans, et al., Impact Damage in Brittle Materials in the Elastic-Plastic Response Regime, Proc. R. Soc. Lond. A., 1978, 361:343-365.

Marouani, et al., Repair and Restoration of the Optical Properties of Sandblasted Glasses by Silica-Based Sol-Gel Coatings, International Journal of Applied Glass Science, 2015, 6(1):94-102.

Nishioka, et al., Sandblasting Durability of Acrylic and Glass Fresnel Lenses for Concentrator Photovoltaic Modules, Solar Energy, 2012, 86(10):3021-3025.

Vandenberghe, et al., Star Shaped Crack Pattern of Broken Windows, Physical Review Letters, 2013, 110(17):174302, 5 pages.

Vermorel, et al., Radial Cracks in Perforated Thin Sheets, Physical Review Letters, 2010, 104(17):175502-1 thru 175502-4.

Yip, Laser Damage Thresholds of Several Metal-Containing Acrylic Polymers at Four Different Wavelengths, Mat. Res. Soc. Symp. Proc., 1992, 236:501-506.

Zener, The Intrinsic Inelasticity of Large Plates, Physical Review, 1941, 59:669-673.

International Search Report and Written Opinion for related International Application No. PCT/US2017/030033, dated Jul. 27, 2017.

\* cited by examiner

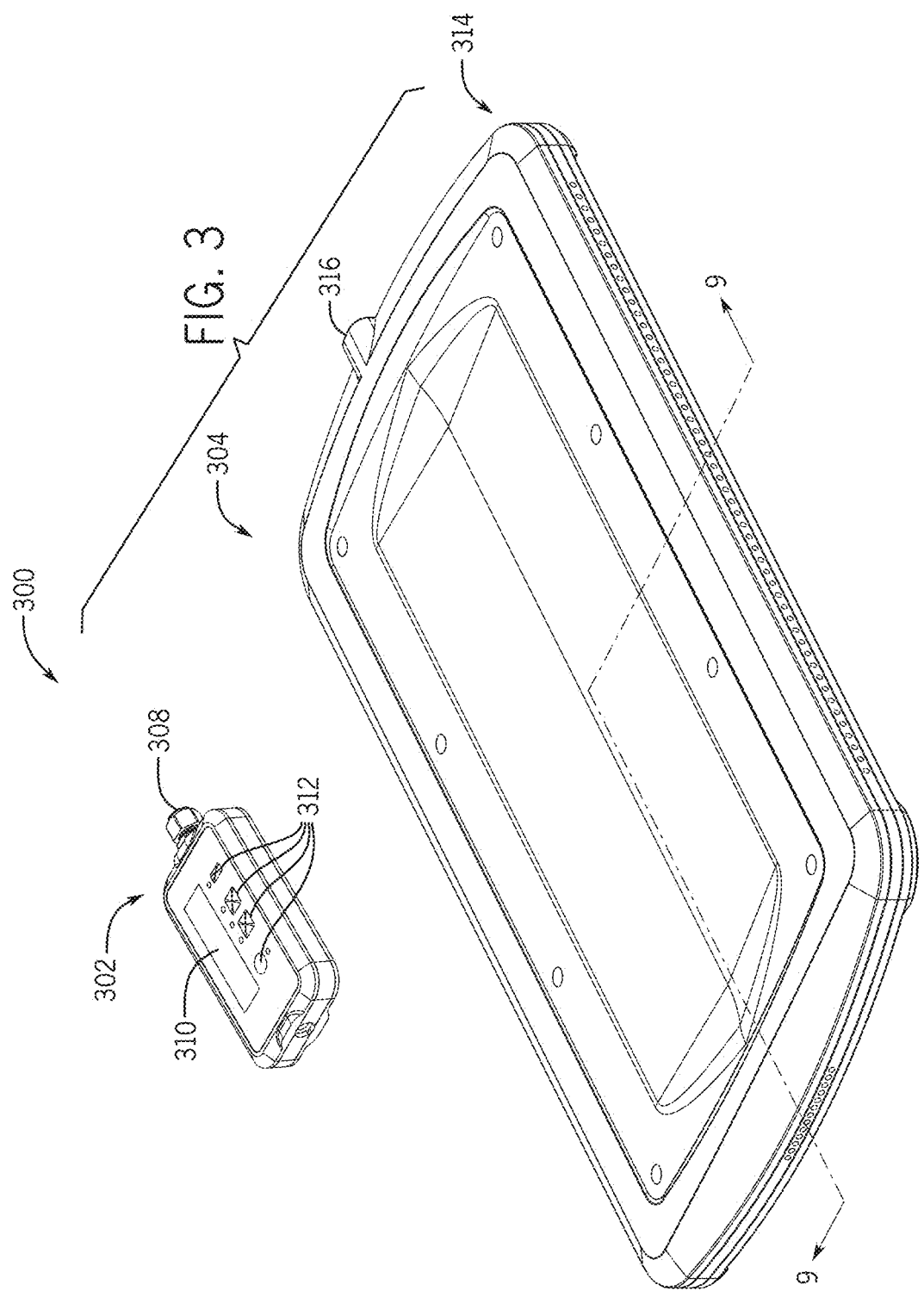

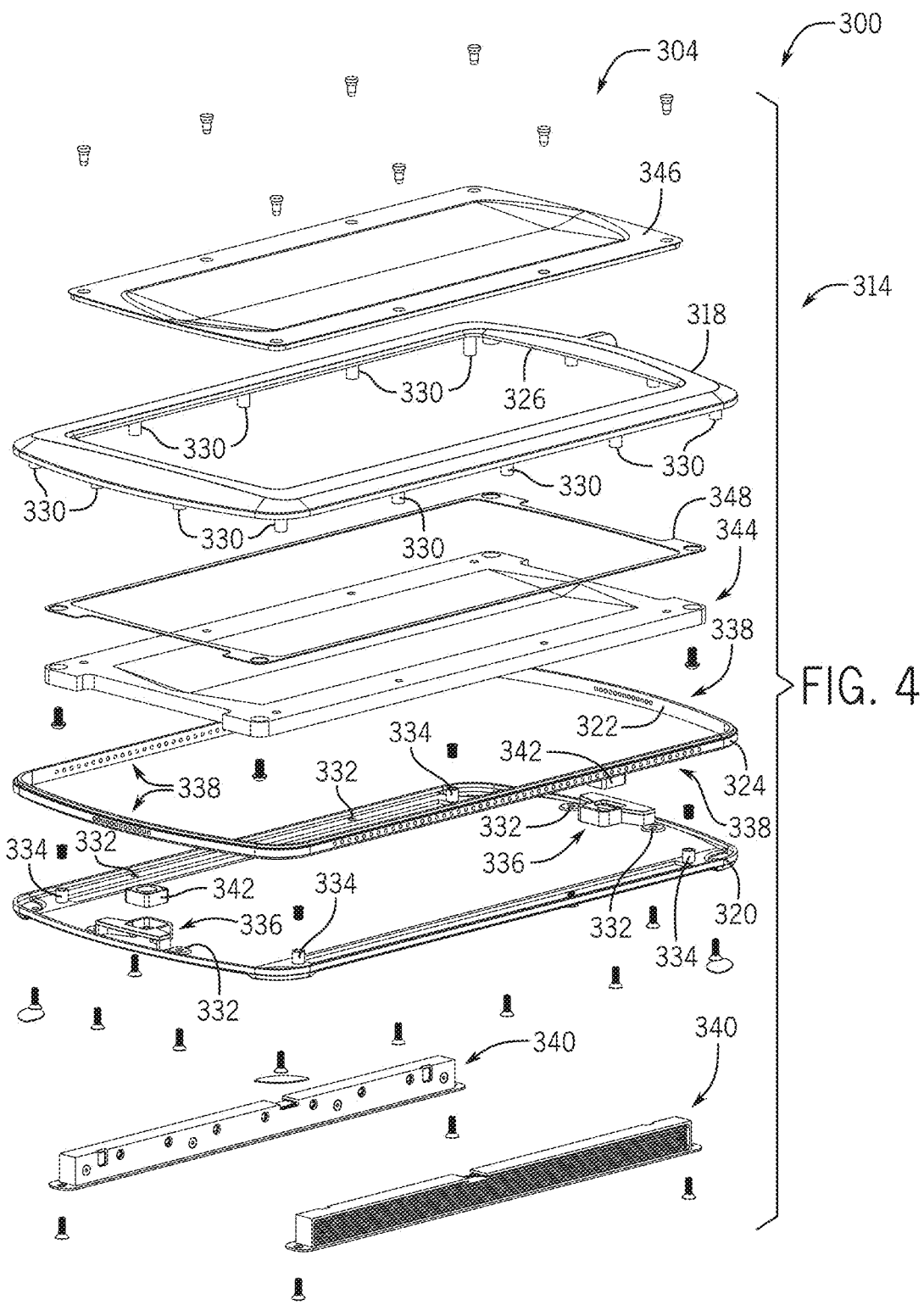

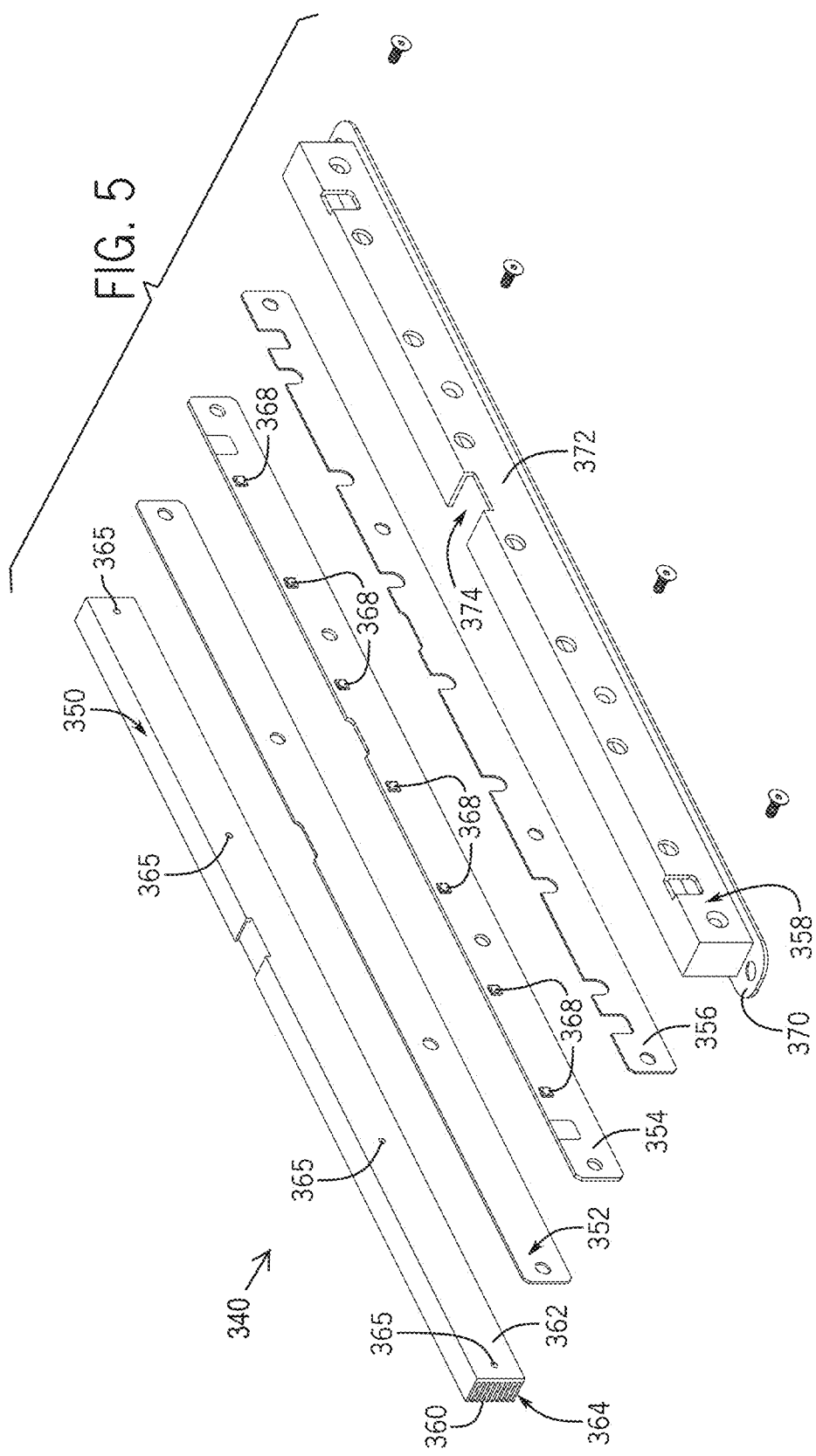

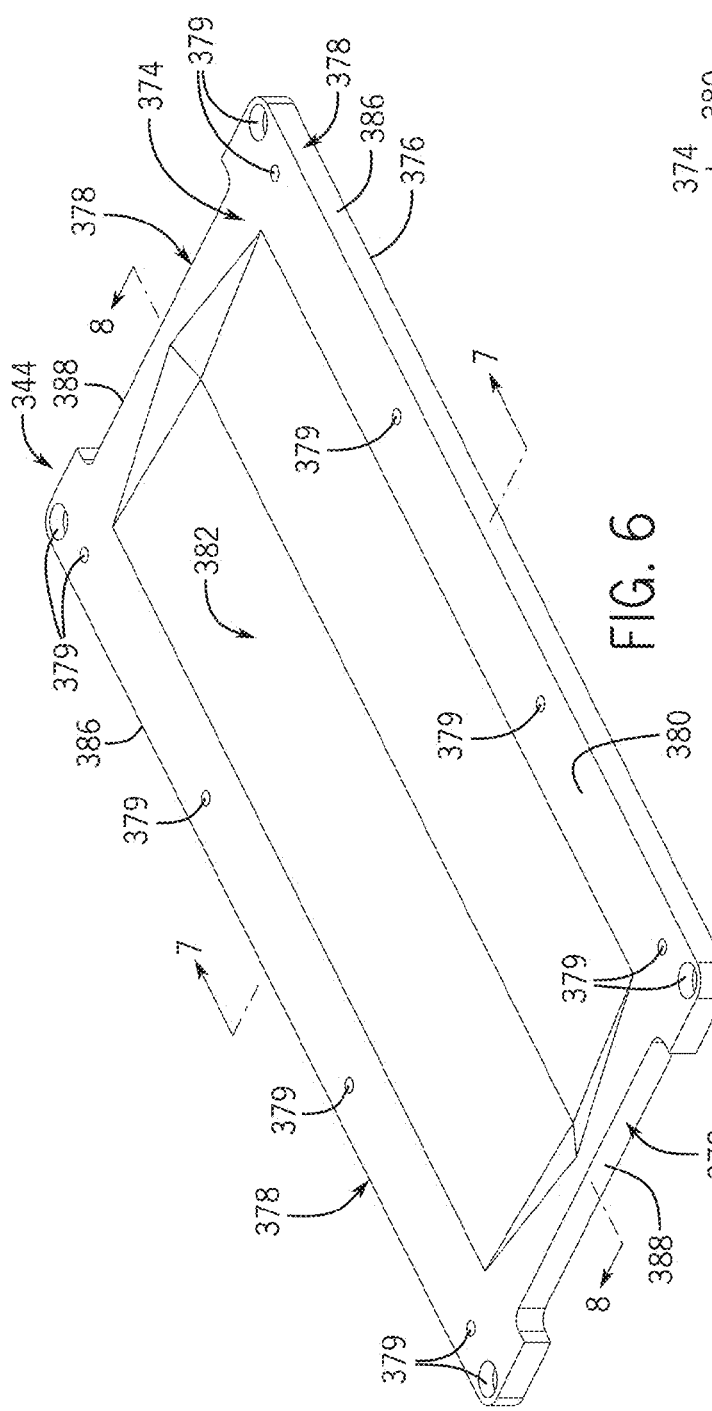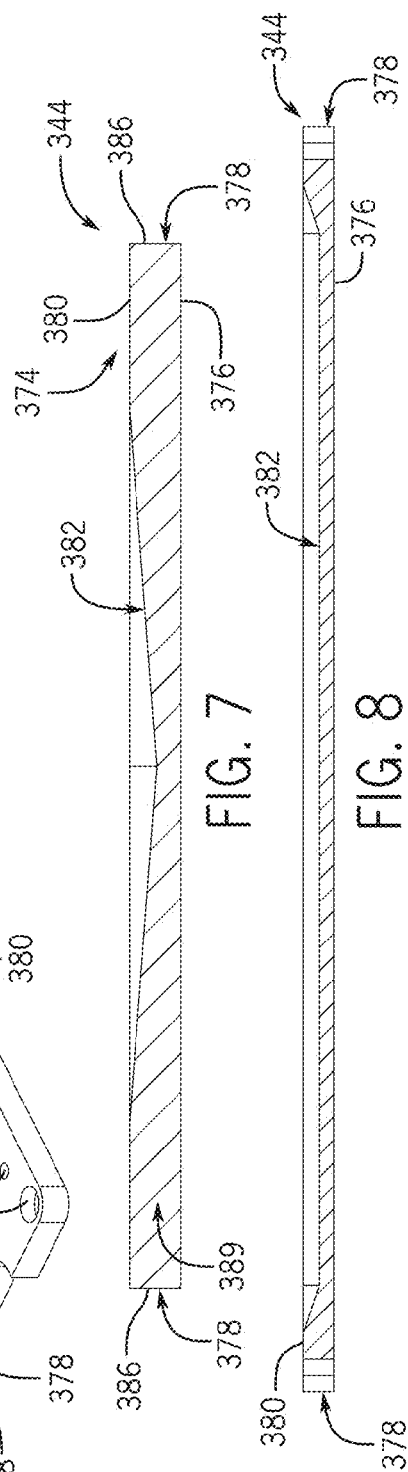

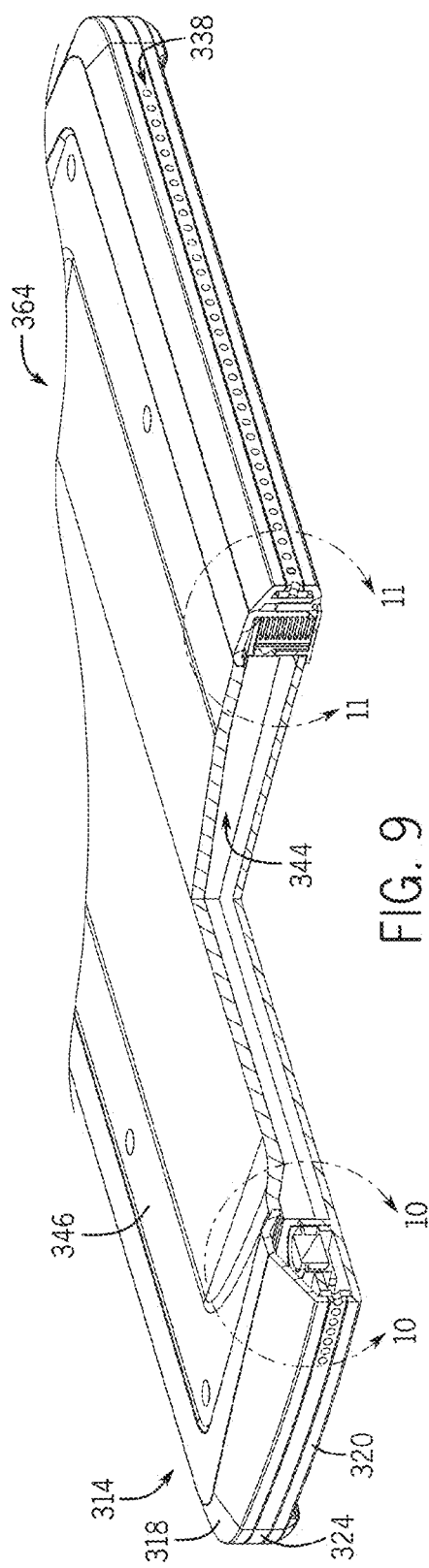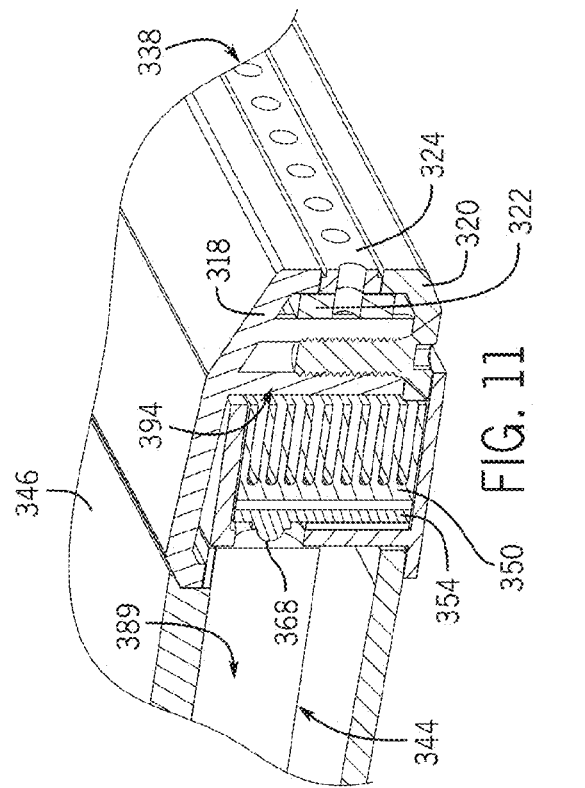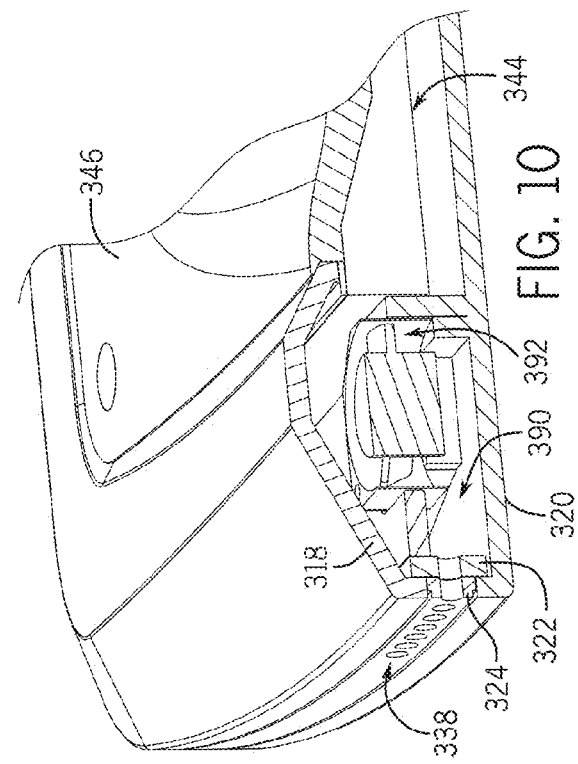

PHOTOTHERAPY APPARATUSES AND METHODS

CROSS-REFERENCES TO RELATED APPLICATIONS

Not Applicable.

STATEMENT REGARDING FEDERALLY SPONSORED RESEARCH

Not Applicable.

BACKGROUND

The present disclosure relates generally to phototherapy and, more specifically, to apparatuses and methods for effectively administering phototherapy.

One instance where phototherapy is utilized is the treatment of jaundice. It is fairly common for neonates to be born clinically jaundiced. Jaundice, or hyperbilirubinemia, results from increased production and transiently impaired elimination of the pigment bilirubin. Neonates affected by jaundice can show persistent high levels of unconjugated bilirubin. High levels of unconjugated bilirubin can lead to kernicterus, a condition involving deposition of bilirubin in the brain, which leads to deficits in cognition, neuromuscular tone and control, and hearing, and even death. The most common therapy for neonatal hyperbilirubinemia or jaundice is phototherapy. The efficacy of phototherapy can depend on irradiance (light intensity), spectral range (light wavelength), exposed skin surface area (Body Surface Area (BSA)), and duration of exposure. Other instances where phototherapy may be used are psoriasis, atopic dermatitis, eczema, and acne vulgaris, to name a few.

BRIEF SUMMARY

The present disclosure provides phototherapy apparatuses and methods. In particular, the present disclosure provides phototherapy apparatuses configured to diffusely transmit light emitted from a light source to a target surface and thereby to a patient.

In one aspect, the present disclosure provides a phototherapy treatment apparatus including a bed having (i) at least one of a transparent or a translucent material, and (ii) a surface having a plurality of microstructures. The phototherapy treatment apparatus further includes a housing holding the bed, and a light source supported by the housing. The light source is constructed and arranged to generate light that is transmitted from the light source through the transparent or translucent material of the bed and through the plurality of microstructures such that the light exits the plurality of microstructures having a more diffusive distribution, thereby enhancing the treatment of an ailment when a patient is lying on the bed.

In another aspect, the present disclosure provides a phototherapy treatment apparatus including a bed having (i) at least one of a transparent or a translucent material, and (ii) a surface having a plurality of microstructures. The phototherapy treatment apparatus further includes a light source constructed and arranged to generate light that is transmitted from the light source through the transparent or translucent material of the neonate bed and through the plurality of microstructures such that the light exits the plurality of microstructures having a more diffusive distribution, thereby enhancing the treatment of an ailment when a patient is lying on the bed.

In yet another aspect, the present disclosure provides a phototherapy treatment method including placing a patient on a bed having at least one of a translucent or transparent material, generating light from a light source; and transmitting the generated light through the material of the bed and through a plurality of microstructures located on a surface of the bed such that the light exits the plurality of microstructures having a more diffusive distribution so as to enhance the treatment of an ailment of the patient placed on the bed.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

FIG. 3 is a perspective view of a phototherapy treatment apparatus according to another non-limiting example of the present disclosure.

FIG. 4 is an exploded view of a bed assembly of the phototherapy treatment apparatus of FIG. 3.

FIG. 5 is an exploded view of an LED module assembly of the phototherapy treatment apparatus of FIG. 3

FIG. 6 is a perspective view of a bed of the phototherapy treatment apparatus of FIG. 3.

FIG. 7 is a cross-sectional view of the bed of FIG. 6 taken along line 7-7.

FIG. 8 is a cross-sectional view of the bed of FIG. 6 taken along line 8-8.

FIG. 9 is a cross-sectional view of a bed assembly of the phototherapy treatment apparatus of FIG. 3 taken along line 9-9.

FIG. 10 is a zoomed in view of the section of FIG. 9 indicated by line 10-10.

FIG. 11 is a zoomed in view of the section of FIG. 9 indicated by line 11-11.

DETAILED DESCRIPTION

The use of the term "light" herein is a term that is synonymous with "electromagnetic radiation," and is not meant to be limited to a specific wavelength range within the electromagnetic spectrum unless specifically stated.

Current phototherapy approaches for treating jaundice in neonates use a fluorescent lamp, a halogen lamp, or LED's, which shine light directly on the neonate. The light sources are typically kept a specified distance away from the neonate (e.g., at least 35 cm) and mounted on top of neonatal bassinets, incubators and/or warmers. The American Association of Pediatrics (AAP) requires that phototherapy devices used to treat jaundiced neonates output an average light intensity of 30 $\mu W/cm^2$/nm, and that the ratio between the minimum and maximum light intensity be greater than 0.4 These approaches suffer from a number of shortcomings, such as: 1) causing the neonate to lose body water due to warming of the ambient air around; 2) potentially exposing the neonate's naked eye to the treatment light; 3) distributing the light intensity unevenly on the BSA; and 4) requiring additional space in neonatal intensive care units ("NICU"). Currently available equipment also has relatively high power requirements and occupy a lot of space, rendering the equipment unsuitable for use in remote places of developing countries and make it expensive to ship.

It would therefore be desirable to have portable phototherapy apparatuses that are configured to efficiently output uniform, or diffusive light irradiance to a patient. Additionally, the portability of the apparatuses can enable at home treatment. It would also be desirable for such phototherapy apparatuses that consume less power, which translates to less heat produced by light sources/equipment and enables more efficient heat dissipation. Further, less heat produced can aid in preventing dehydration while treating the patient. As will be described below, apparatuses described herein facilitate a reduction in a gap between a light source and a patient, and use a controllable medium to channel light thereby achieving power requirements that are fractional when compared with the prior art.

Figure 1:
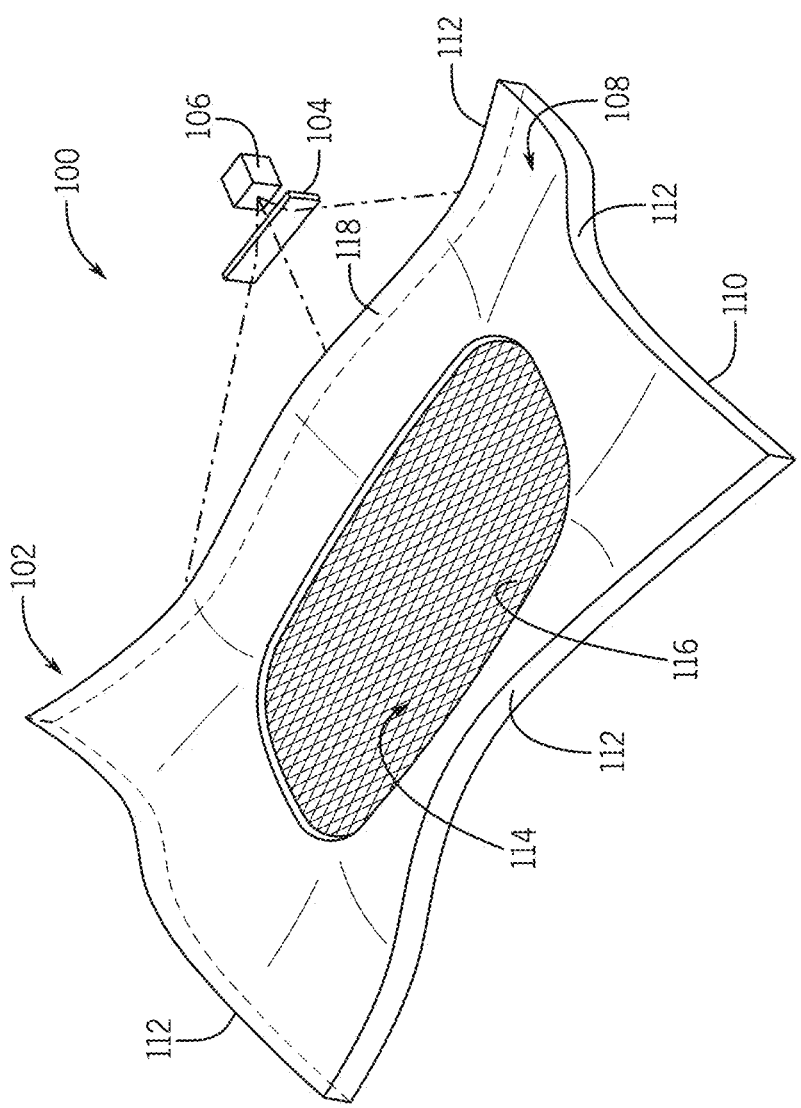
FIG. 1 is a perspective view of a phototherapy treatment apparatus according to one non-limiting example of the present disclosure.

FIG. 1 illustrates a perspective view of one non-limiting example of a phototherapy treatment apparatus 100 of the present disclosure. The phototherapy treatment apparatus 100 includes a bed 102, a transition device 104, and a light source 106. The bed 102 includes a top side 108, a bottom surface 110, and a plurality of side surfaces 112. The bed 102 may include a material that is transparent and/or translucent to electromagnetic radiation in the visible spectrum and its neighborhood (e.g., between approximately 100 nanometers (nm) and 900 nm). Bed 102 may additionally include a material having a higher refractive index than air. Example materials for bed 102 include one or more polymer, such as, polycarbonate (PC), polymethyl methacrylate (PMMA) and/or polystyrene (PS).

The top side 108 of the bed 102 includes a treatment surface 114 configured to diffusely transmit light emitted from light source 106 to a neonate or patient positioned on the top side 108. The diffuse transmission characteristics of the treatment surface 114 may be obtained by mechanical, chemical, or photic processes that produce microstructures 116 on the treatment surface 114. The microstructures 116 may comprise, for example, discolored char particles, voids, and/or micro-cracks. The individual or collective action of these voids, micro-cracks, chars, or any other suitable microstructures can be responsible for diffusely scattering radiation transmitted from the treatment surface 114 through the microstructures 116. Examples of processes that may be used to create microstructures 116 include one or more of CNC machining, laser engraving, sand blasting, chemical engraving, and/or other suitable mechanical, chemical, or photic operations. Alternatively or additionally, the microstructures 116 may be formed on a thin layer than can be coated or embedded on the treatment surface 114. The plurality of side surfaces 112 of the bed 102 includes an incident surface 118, which is configured to receive the light emitted from light source 106.

In some non-limiting examples, light source 106 may be configured to emit light in a broadband spectrum spanning between, but not limited to, the ultraviolet and infrared spectrums. In these non-limiting examples, the light source 106 may be in the form of a lamp or solar radiation. In other non-limiting examples, light source 106 may be configured to emit light in a narrow band in the visible spectrum and its neighborhood (e.g., between approximately 100 nm and 900 nm). In these non-limiting example, the light source 106 may be in the form of a light emitting diode (LED) or a laser. In some non-limiting examples, the light source 106 may be configured to emit light that are focused towards a specific phototherapy application. For example, the light source 106 may be configured to emit light at a wavelength, or range of wavelengths, capable of photodissociating bilirubin in the blood of a patient (e.g., a neonate). Alternatively or additionally, the light source 106 may be configured to emit light between approximately 280 nm and 320 nm for treating eczema, atopic dermatitis, vitiligo, and/or psoriasis. Alternatively or additionally, the light source 106 may be configured to emit visible light to facilitate treating seasonal affective disorder and/or bipolar disorder. Alternatively or additionally, the light source 106 may be configured to emit light between approximately 100 nm and 280 nm for treating wound healing and/or inhibiting bacterial growth. Alternatively or additionally, the light source 106 may be configured to emit infrared light for treating hypothermia. It should be appreciated that the phototherapy treatments listed above are not meant to be limiting in any way and the light source 106 can be configured to emit light to facilitate phototherapy treatments for a variety of ailments.

In operation, light emitted from light source 106 travels through the transition device 104 to incident surface 118. The transition device 104 can be used to serve one or more functions including, but not limited to, transmitting the light from the light source 106 to the incident surface 118, focusing, scattering, or diffusing the light, shifting the wavelength of the light emitted from the light source 106, filtering the light to pass only a specific bandwidth of wavelengths through, and/or amplifying the intensity of the light. In one non-limiting example, after passing through the transition device 104, the light emitted from light source 106 is filtered to a wavelength capable of photodissociating bilirubin to treat a jaundiced patient. In another non-limiting example the transition device 104 may focus the light along a substantial portion or, the entire length, of incident surface 118. In still other non-limiting examples, the light emitted from the light source 106 can be filter to a wavelength capable of treating psoriasis, bipolar disorder, eczema, and SAID, to name a few.

Figure 2:
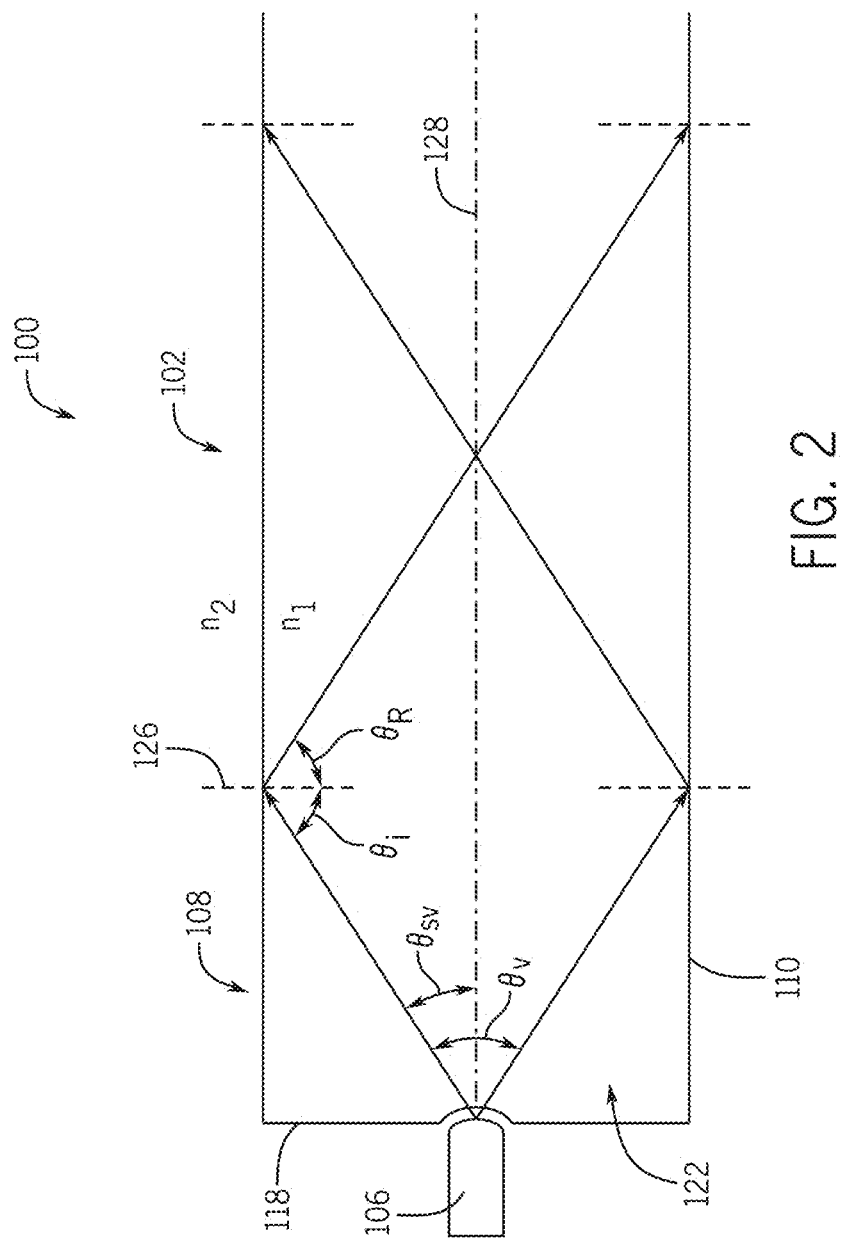
FIG. 2 is a cross-sectional view of a bed of the phototherapy treatment apparatus of FIG. 1 illustrating light traveling through a light channel of the bed, according to one aspect of the present disclosure.

As shown in FIG. 2, once the light (shown as light rays) emitted from the light source 106 reaches the incident surface 118, the light transmits through the incident surface 118 and enters a light channel 122 defined between the top side 108 and the bottom surface 110 of the bed 102. The light that enters the light channel 122 can be emitted into the light channel 122 at a viewing angle $\theta_v$ such that total internal reflection (TIR) is achieved, as described below.

There are two conditions for TIR to occur: (1) light should travel from denser to rarer medium (i.e., from a higher index of refraction to a lower index of refraction), and (2) an angle of incidence in the denser medium should be greater than a critical angle. As described above, bed 102 can be fabricated from a material with a higher index of refraction than air. Bed 102 therefore satisfies the first condition for TIR. The second constraint can be satisfied by proper design of the viewing angle $\theta_v$ defined by the light entering the light channel 122 and the specific material from which the bed 102 is fabricated. According to the second condition, TIR can be achieved when light traveling through the light channel 122 intersects a medium boundary surface 124 formed between either the top surface 108 or the bottom surface 110 and the air at an angle of incidence $\theta_i$ larger than a critical angle $\theta_{critical}$ (i.e., $\theta_i > \theta_{critical}$). The critical angle $\theta_{critical}$ is measured with respect to an axis 126 normal to the medium boundary surface 124. The critical angle $\theta_{critical}$ is determined based on the index of refraction of air $n_2$ and the index of refraction of the bed material $n_1$, in accordance with Snell's law shown below.

$$\theta_{critical} = \arcsin\left(\frac{n_2}{n_1}\right) \quad (1)$$

The angle of incidence $\theta_i$ can be related to a semi-viewing angle $\theta_{sv}$, defined by the light traveling in the light channel 122, by:

$$\theta_i = 90 - \theta_{sv}. \quad (2)$$

Substituting in the constraint that $\theta_i > \theta_{critical}$, the semi-viewing angle $\theta_{sv}$ can be related to the critical angle $\theta_{critical}$ by:

$$\theta_{sv} < 90 - \arcsin\left(\frac{n_2}{n_1}\right). \quad (3)$$

As shown by the illustrated non-limiting example of FIG. 2 and as described by equations 1-3, light enters the light channel 122 of the bed 102 at a viewing angle $\theta_v$, generally defined as an off-axis angle from a centerline 128, defined by the light source 106, where the luminous intensity is approximately half of a peak value. The viewing angle θv can be divided into two semi-viewing angles $\theta_{sv}$, both measured between the light and the centerline 128 of the light source 106. The centerline 128 can be parallel to the top surface 108, and the axis 126, which is normal to the top and bottom surfaces 108, 110, forms a right angle with the central-horizontal axis 128. As such, due to geometrical constraints, the angles of incidence $\theta_i$, formed between the outermost light and the axis 126, are complementary to the corresponding semi-viewing angles $\theta_{sv}$ (each semi-viewing angle added to the corresponding angle of incidence would equal a right angle). Therefore, each angle of incidence θi is equal to ninety degrees minus the corresponding semi-viewing angle $\theta_{sv}$. To ensure that TIR is achieved, ninety degrees minus the corresponding semi-viewing angle $\theta_{sv}$ is maintained below the critical angle $\theta_{critical}$, as determined by the equations 1-3 above. Thus, once the index of refraction of the bed 102 material is known, a minimum viewing angle $\theta_v$ for the light entering the light channel 122 can be defined to ensure TIR.

It should be appreciated that the example described above with reference to FIG. 2 do not account for when the centerline 128 of the light source 102 is not parallel to the top surface 108 and/or the bottom surface 110. In such a case, a tilt angle $\theta_{tilt}$ can be defined as the angle between the centerline 128 of the light source 106 and a central-horizontal axis defined between the top surface 108 and the bottom surface 110. The semi-viewing angle of equation 3 can be modified to account for the tilt angle $\theta_{tilt}$, as defined below.

$$\theta_{sv} < (90 + \theta_{tilt}) - \arcsin\left(\frac{n_2}{n_1}\right) \quad (4)$$

The TIR achieved through the light channel 122 of the bed 102 ensures that a maximum intensity of light can be delivered to a patient on the treatment surface 114 with minimal losses due to refraction. Alternatively or additionally, the bed 102 may be coated, except on the treatment surface 114 and the incident surface 118, with an reflective backing to further prevent light leakage from the light channel 122. The TIR can be maintained throughout the light channel 122 until the light contacts one or more of the plurality of microstructures on the treatment surface 114. After contacting one or more of the plurality of microstructures on the treatment surface 114, the light can be diffusely transmitted from the treatment surface 114 to a patient positioned on the treatment surface 114. In this way, the phototherapy treatment apparatus 100 is configured to efficiently transmit treatment light from the light source 106 to a patient positioned on the treatment surface 114 such that the treatment light transmitted to the patient defined a generally uniform, or diffuse, profile. The efficient transmission of light through the light channel 122 of the bed 102 to the treatment surface 122 enables the phototherapy treatment apparatus 100 to consume less power, which translates to less heat produced by the light sources 106, and enables more efficient heat dissipation and lower power requirements.

FIGS. 3-12 illustrate another non-limiting example of a phototherapy treatment apparatus 300 of the present disclosure. Referring to FIG. 3, the phototherapy treatment apparatus 300 includes a control unit 302 in communication with a bed assembly 304. Control unit 302 includes a port 308 configured to be in communication with the bed assembly 304, a display 310, and a keypad 312. The port 308 can be in direct wired communication with bed assembly 304, or in wireless communication with bed assembly 304. Display 310 is configured to display operational data of the bed assembly 304 (e.g., total treatment time, treatment time remaining, temperature, light intensity, alarms, etc.). Keypad 312 is configured to control certain operating parameters of the bed assembly 304, as described below. It should be appreciated that control unit 302 includes electronics that enable a user to control the operating parameters of the bed assembly 304.

The bed assembly 304 includes a housing 314 and an input 316 for receiving power (e.g., power from an AC or DC power source). In the illustrated non-limiting example, the phototherapy treatment apparatus 300 defines a substantially cuboid shape. In other non-limiting examples, the phototherapy treatment apparatus 300 may define another polyhedron shape, or any other suitable shape that is deemed appropriate for supporting a patient and allowing light to treat the patient.

Turning to FIG. 4, the housing 314 of the bed assembly 304 includes a top plate 318 and a bottom plate 320 spaced apart such that both an inner connector plate 322 and an outer connector plate 324 can be arranged between the top and bottom plates 318 and 320. The top plate 318 defines a central opening 326 dimensioned to receive a cover pad 346, and may include the input 316 and a plurality of fastener receiving columns 330. The bottom plate 320 includes a plurality of plate mounting apertures 332, a plurality of LED module mounting apertures 334, and two opposing fan housings 336. Each of the plurality of plate mounting apertures 332 are configured to align with a corresponding one of the fastener receiving columns 330 of the top plate 318. When assembled, a fastening element can be received by each of the plurality of plate mounting apertures 332 and threaded into the corresponding fastener receiving column 330 thereby fastening the top plate 318 to the bottom plate 320. In the illustrated non-limiting example, the top 318 and bottom plates 320 may be coupled using a plurality of fasteners. In other non-limiting examples, the top 318 and bottom 320 plates may be coupled, for example, by an adhesive or any other suitable coupling mechanism.

The inner and outer connector plates 322 and 324 each include a plurality of cooling apertures 338 defining a vent. In an embodiment, cooling apertures 338 are arranged around a periphery of the plates 322, 324 and allow air flow between the housing 314 and the surroundings. When assembled (as shown in FIGS. 3 and 9-11), the inner connector plate 322 and the outer connector plate 324 can be fastened between the top plate 318 and the bottom plate 320 with the inner connector plate 322 arranged circumferentially within the outer connector plate 324.

The bed assembly 304 further includes a pair of light emitting diode (LED) modules 340, a pair of fans 342 received within the two opposing fan housings 336 of the bottom plate 320, a bed 344, the pad or cover pad 346, and a bed gasket 348. The pad 346 may be fabricated in an example embodiment from a silicone material and can be configured to provide a soft and comfortable surface for the neonate. Additionally, pad 346 can be configured to transmit the light emitted from the pair of LED modules 340 and may act as a buffer to balance out light intensity variations across the bed 344. Further, the pad 346 can act as a seal to prevent liquids from entering, and potentially damaging, the internal components within the housing 314. In another non-limiting example, the pad 346 may be integrated into the bed 344. The bed gasket 348 is dimensioned to be arranged around a periphery of the bed 344 and can be arranged between the bed 344 and the pad 346. The bed 344 and the pad 346 are further dimensioned such that a periphery of the pad 346 is in contact with the top plate 318, such that the center of the pad 346 is accessible through the central opening 326 of the top plate 318.

It should be appreciated that each of the pair of LED modules 340 can include similar components. The following description therefore can apply to each of LED modules 340. With reference to FIG. 5, each pair of LED modules 340 includes a heat sink 350, a thermal interface 352, an LED printed circuit board 354, a spacer plate 356, and a module housing 358. The heat sink 350 includes a finned side 360 and a non-finned side 362. The finned side 360 includes a plurality of fins 364 to provide the heat sink 350 with a greater surface area and thereby provide improved heat dissipation from the printed circuit board 354 during operation. The non-finned side 362 includes a plurality of threaded apertures 365 spaced along a length of the heat sink 350.

The thermal interface 352 is arranged between the heat sink 350 and the printed circuit board 354, and is dimensioned to increase a contact surface area and improve heat transfer from the printed circuit board 354 to the heat sink 350. The printed circuit board 354 is arranged between the thermal interface 352 and the spacer plate 356, and includes a non-LED side (not shown) and an LED side 366. When assembled, the non-LED side engages the thermal interface 352 and the LED side 366 engages the spacer plate 356. The LED side 366 includes a plurality of LEDs 368 incrementally spaced along a length of the printed circuit board 354. The spacer plate 356 is arranged between the printed circuit board 354 and the module housing 358. The module housing 358 includes a mounting flange 370, a bed mating surface 372, and a housing recess 374. The bed mating surface 372 is arranged to engage with the bed 344 when the bed assembly 304 is assembled. The housing recess 374 is configured to receive the heat sink 350, the thermal interface 352, the printed circuit board 354, and the spacer plate 356.

Each of the thermal interface 352, the printed circuit board 354, the spacer plate 356, and the module housing 358 includes a plurality of mounting apertures that align with the plurality of threaded apertures 365 of the heat sink 350. When the pair of LED modules 340 are assembled, a fastening element (e.g., a threaded bolt or screw) can be inserted through the plurality of mounting apertures formed in the thermal interface 352, the printed circuit board 354, the second spacer plate 356, and the module housing 358. The fastening elements can then be threaded into the plurality of threaded apertures 365 to secure the heat sink 350, thermal interface 352, the printed circuit board 354, and the spacer plate 356 within the module housing 358.

Turning to FIGS. 6-8, the bed 344 includes a top side 374, a bottom side 376, a plurality of side surfaces 378, and a plurality of mounting apertures 379. The plurality of mounting apertures 379 can be configured to receive a fastening element (as shown in FIG. 4) to couple the bed 344 to the pad 346 and also to couple the bed 344 to the bottom plate 320. The top side 374 of the bed 344 includes a peripheral surface 380 and a treatment surface 382. The treatment surface 382 includes a plurality of microstructures 384 (shown in FIG. 12) and can define a substantially concave shape or concave channel. The concave shape defined by the treatment surface 382 can be dimensioned such that, when a patient is placed onto the treatment surface 382 during operation, light emitted from the treatment surface 382 are focused at an angle, increasing body exposure to the light, as described in detail below. In other non-limiting examples, the treatment surface 382 may define an alternative shape, for example a flat shape, as desired.

The plurality of microstructures 384 can be generally defined as purposefully placed imperfections, capable of dispersing light. In operation, it is desirable to have the treatment surface of bed 344 transfer light from within the bed 344 to the patient (e.g., a neonate) over a wide range of angles to maximize BSA and over a generally uniform, or diffuse, gradient flux. The plurality of microstructures 384 enable the bed 344 to provide such generally uniform or diffuse gradient flux. Bed 344 is also easily manufactured because processes for making the bed can be easily automated. The plurality of microstructures 384 can again be voids, micro-cracks, chars, any combination thereof, or any other suitable microstructures capable of dispersing light, and can be formed by one or more of CNC machining, laser engraving, sand blasting, chemical engraving, or any other suitable mechanical, chemical, or photic operations, as will be described in detail below.

Two of the plurality of side surfaces 378 in the illustrated non-limiting example are incident surfaces 386, which receive incident jaundice treatment light from the plurality of LEDs 368 during operation, as described in detail below. The other two of the plurality of side surfaces 378 include fan clearance recesses 388 to allow clearance for the two opposing fan housings 336 of the bottom plate 320. A light channel 389 can be defined between the top side 374 and the bottom side 376 along which light can travel from one of the incident surfaces 386 to the other incident surface 386. In some non-limiting examples, one or more of the bottom side 376, the peripheral surface 380, and the side surface 378 which are not incident surface 386 may be covered with an anti-reflection coating or material configured to reflect light emitted by the plurality of LEDs 368.

Turning to FIGS. 9-11, the fan housing 336 further defines an fan chamber 390 and a fan recess 392, which receives the fan 342 within the fan housing 336. With reference to FIG. 11, when LED modules 340 are assembled within the housing 314, each LED module 340 is arranged such that the bed mating surface 372 of the module housing 358 sits flush with the incident surface 386 of the bed 344. In this arrangement, the plurality of LEDs 368 of the LED printed circuit board 354 can directly emit jaundice treatment light onto the incident surface 386 during operation. Also, this arrangement can align the plurality of LEDs 368 with a centerline 395 defined by the light channel 389.

An air passageway 394 is formed between the heat sink 350 of the LED module 340 and the inner connector plate 322. The air passageway 394 extends around the bed 344 within the housing 314 to facilitate air flow. The finned sides 360 of the heat sinks 350 border this air passageway 394, allowing the plurality of fins 364 to transfer heat, either passively or actively, away from the LED module 340 and into the air passageway 394. In the illustrated non-limiting example, during operation, the fans 342 provide air flow that flows between the surroundings through the cooling apertures 338 and to the air passageway 394. This allows the heat sink 350 to more efficiently transfer heat away from the LED module 340. It should be appreciated that in some non-limiting examples, the bed assembly 304 may not include the fans 342 and the heat sinks 350 may be sufficient to passively cool the printable circuit boards 354.

Figure 12:
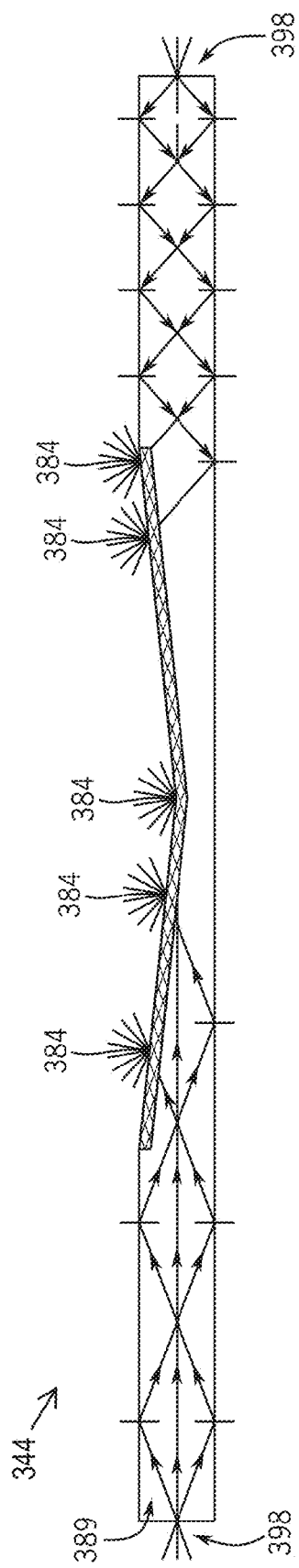
FIG. 12 is a cross-sectional view of the bed of FIG. 6 illustrating light traveling through a light channel of the bed and being dispersed by a plurality of microstructures on treatment surface of the bed, according to one aspect of the present disclosure.

FIG. 12 is a schematic diagram illustrating a non-limiting example of the jaundice treatment light traveling through the light channel 389 of the bed 344. In FIG. 12, the jaundice treatment light have been generated by a light source and are illustrated as light rays 398 that are emitted at a viewing angle such that TIR is achieved. That is, a viewing angle defined by the LEDs 368 can be sufficient to ensure that TIR occurs through the light channel 389, as illustrated in FIG. 2 and defined by equations 1-3 above.

The light rays 398 transmitting through light channel 389 are totally internally reflected between the top and bottom sides 374, 376 of the bed 344 several times before reaching treatment surface 382. At treatment surface 382, the light rays 398 are transmitted through the microstructures 384 such that the light rays exit the microstructures 384 with a more diffusive distribution than the light rays 398 that entered the microstructures. That is, the light rays are generally evenly dispersed by the plurality of microstructures 384 in all directions above the light channel 389 thereby providing a diffuse profile at the treatment surface 382. Although the illustrated non-limiting example shows light rays 398 emitted at two different viewing angles, in other non-limiting examples, the light rays 398 may be emitted at the same or different viewing angles to suit operational conditions.

As shown in FIG. 12, the plurality of microstructures 384 can intercept the light traveling through the light channel 389 on its natural trajectory and disperse it to prevent TIR along the treatment surface 382. The plurality of microstructures 384 serve the purpose of making the angle of incidence, $\theta_i$, less than the critical angle $\theta_{crit}$. As described above, some of the commonly used methods to induce surface irregularities, or microstructures, comprise machining, chemical etching, and laser etching. Irrespective of the method of manufacture, kinetic and thermal energy of the incident particles can be highly relevant parameters to explain the damage (i.e., the formation of microstructures). The impacting particles of mechanical operations can be described through kinetic energy dissipated during an erosion process, and the impacting particles in photic and chemical processes can be described through thermal energy.

Material impacted by a projectile is subject to plastic deformation and/or fracture. The types of fracture—radial, circumferential, lateral, or conical—depend on the size distribution of inherent cracks, a fracture toughness of material, and a magnitude of a dynamic elastic stress field created during impact (kinetic energy of impacting particles). These fractures manifest themselves as cracks, voids, and remnant char particles that are collectively referred to as the plurality of microstructures 384 herein.

Figure 13A:
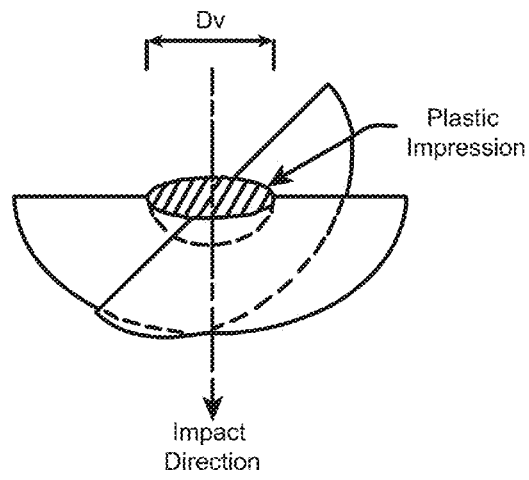
FIG. 13A is an illustration of a radial crack according to one aspect of the present disclosure.
Figure 13B:
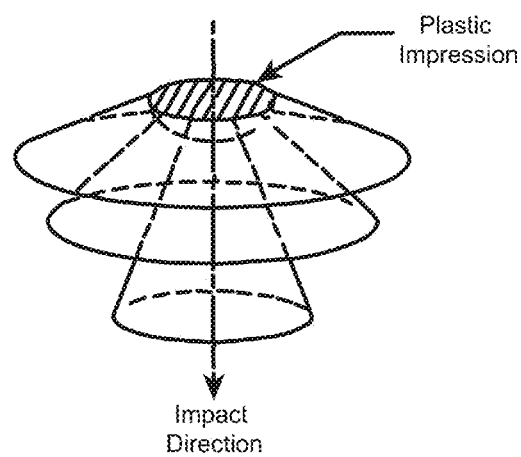
FIG. 13B is an illustration of a conical crack according to one aspect of the present disclosure.
Figure 13C:
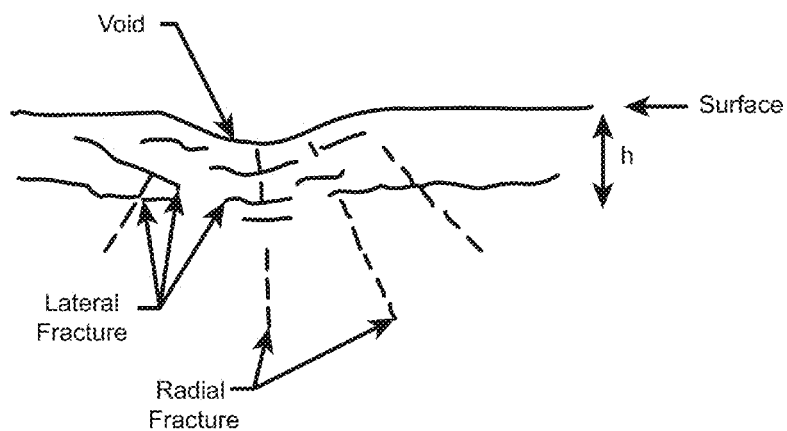
FIG. 13C is an illustration of a lateral crack according to one aspect of the present disclosure.

Cracks may be considered primary microstructures as they grow deeper into the treatment surface 382, during manufacture, and tap into a higher percentage of light flux inside the bed 344. Cracks can be divided into three categories namely radial cracks, lateral cracks, and conical cracks, as shown in FIGS. 13A-C. Radial cracks (FIG. 13A) extend from voids and, at any given time, they can have approximately the same length. Conical cracks (FIG. 13B) may dominate in softer materials due to plastic deformation, but can appear in the form of circumferential cracks in harder materials. Lateral cracks (FIG. 13C) may be formed after the penetration has terminated, deriving from the relatively large in-plane tensile stresses of the appropriate orientation formed due to the interaction of the plastic wave with the unloading elastic wave.

A number of cracks at an impact site can depend on an impact speed V, and the thickness, h, of the bed 344. Assuming the transverse bending energy can be neglected, as the thickness is small compared to the other dimensions of the bed 344, the number of cracks on the treatment surface 382 can be approximated by:

$$n \approx \left(\frac{Eh}{\Gamma}\right)^{1/3}\left(\frac{V}{c}\right)^{1/2} \quad (5)$$

Where E is the Bulk Modulus, h is a thickness of the bed 344, $\Gamma$ is the fracture energy, V is a velocity of an impact, and c is a velocity of sound in the bed 344. The velocity of an impact V may depend on the specific manufacturing process used to manufacture the treatment surface 382. For example, a CNC operation may be correlated to a speed that the router hits the treatment surface 382 and, for sand blasting, it may be correlated to a speed that the sand hits the treatment surface 382. In some non-limiting examples, the treatment surface 382 of the bed 344 may comprise between approximately 3797 and approximately 6132 cracks per square inch. In other non-limiting examples, there can be more smaller cracks, which can be a result of the machining process, and that can also contribute to light dispersion. In these non-limiting examples, the treatment surface 382 of the bed 344 may comprise greater than approximately 1000 cracks per square inch.

In some non-limiting examples, a length of the cracks formed in the treatment surface 382 during machining may be between approximately 20 micrometers (μm) and 4000 μm, for radial cracks, and a depth of damage can be between approximately 20 μm and approximately 600 μm.

Voids and char particles may be considered as secondary microstructures as their size and shape can be governed by the nature of the projectile (e.g., router, sand, laser beam, or etchant). Voids can be craters left behind from the deformation process. In order to achieve a generally uniform distribution of voids, a balance between the diameter of the voids and their distribution may need to be balanced. Large voids can be undesirable as they alter the topography and might create a new surface without any microstructures. Closely compacted voids can have intertwined cracks, which may make the surface unstable and hot-pots for crack propagation. Keeping the light diffusing capabilities and the usability of the bed 344 in tact, voids on the treatment surface 382 can be between 20 μm and 200 μm in diameter ($D_v$), and should be spaced $2D_v<C_v<10$, where $C_v$ is the center-to-center distance between voids, for minimum interaction between the plurality of microstructures 384 and a diffuse light profile.

Char particles can be characterized as stepped walls surrounding voids. Char particles can be produced by plastic deformation due to the compression waves. In some cases, the char particles collapse and spread over to smoother regions and can affect the interface properties of the treatment surface 382 and act as spots for extracting light (i.e., act as microstructures). In some non-limiting examples, the char particles can be as large as $4D_v$.

Figure 14:
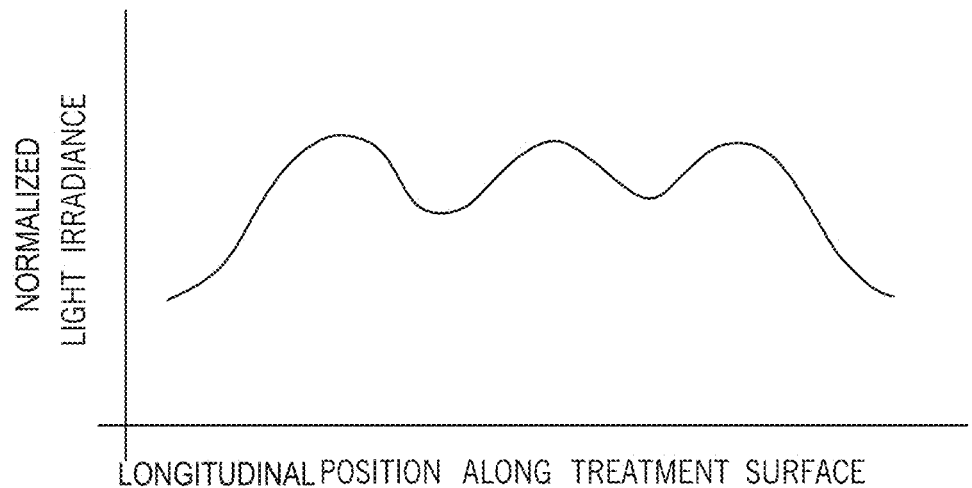
FIG. 14 is a graph illustrating a normalized light irradiance profile as a function of longitudinal distance along a treatment surface without a plurality of microstructures.
Figure 15:
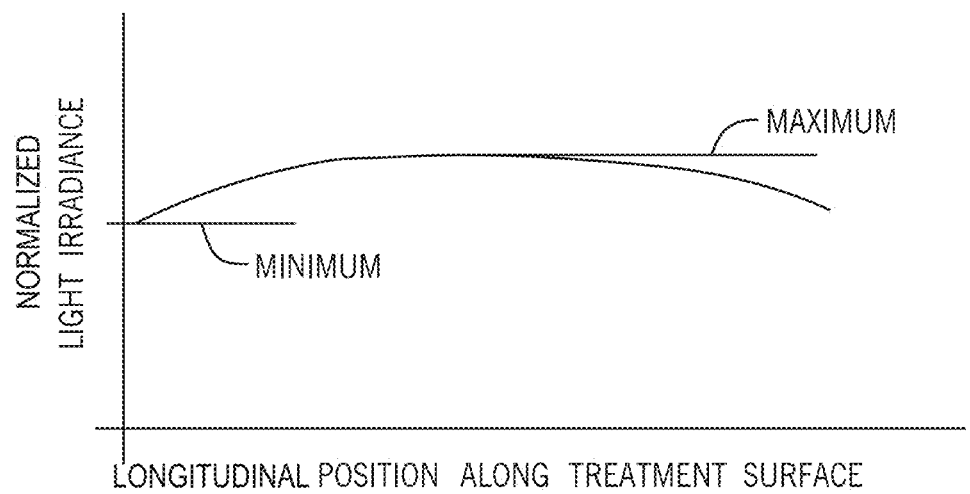
FIG. 15 is a graph illustrating a normalized light irradiance profile as a function of longitudinal distance along a treatment surface with a plurality of microstructures.

Each of the above-described characteristics of the plurality of microstructures 384 can enabled the phototherapy treatment apparatus 300 to provide a diffuse light profile at the treatment surface 384. FIGS. 14 and 15 illustrate one non-limiting example of a more diffuse, or uniform light intensity (or power), profile that can be achieved using the plurality of microstructures 384 of the present disclosure. It should be appreciated that because the plurality of LEDs 368 may not define a continuous light intensity profile along the incident surfaces 386 (i.e., the plurality of LEDs 368 are discretely spaced along the incident surfaces 368) a light irradiance profile may substantially vary as a function of position along the treatment surface 382.

Referring to FIG. 14, FIG. 14 is a graph illustrating a 2D (a cross-sectional) light irradiance profile as a function of longitudinal position along treatment surface 382 without the plurality of microstructures. The peaks in light irradiance correspond with the positions of the plurality of LEDs 368 along the incident surfaces 386. It should be appreciated that a similar light irradiance profile may exist along the light channel 389 as the light is propagating throughout light channel 389.

FIG. 15 is a graph illustrating a 2D light irradiance profile as a function of longitudinal position along the treatment surface 382 with the addition of the plurality of microstructures 384. The light irradiance profile is substantially more diffuse, or more uniform, than the light irradiance profile without the plurality of microstructures 384 as illustrated in FIG. 14, than the light irradiance profile within the light channel 389. Thus, the plurality of microstructures 384 act to diffusely distribute the light irradiance from the plurality of LEDs 368 over the treatment surface 382 thereby increasing an integrated light irradiance output by the phototherapy treatment apparatus 300, which can lead to more efficient phototherapy administration.

The graph of FIG. 15 further illustrates a maximum irradiance and a minimum irradiance output from the treatment surface 382. An irradiance ratio can be defined as a ratio of the minimum irradiance to the maximum irradiance. The TIR provided by the bed 344 and the diffusion provided by the plurality of microstructures 384 act to maximize the irradiance ratio to ensure effective the patient receives a substantially uniform, or diffuse, light irradiance over the entire surface area of the treatment surface 382. Furthermore, it should be appreciated that the irradiance ratio and/or the diffuse profile along the treatment surface 382 can be controlled, for example, by the an angle (taper angle) of the treatment surface 382, a distance between the treatment surface 382 and the plurality of LEDs 368, a width of the light channel 389, a number of the plurality of LEDs 368, and/or a spacing between the plurality of LEDs 368.

Figure 16:
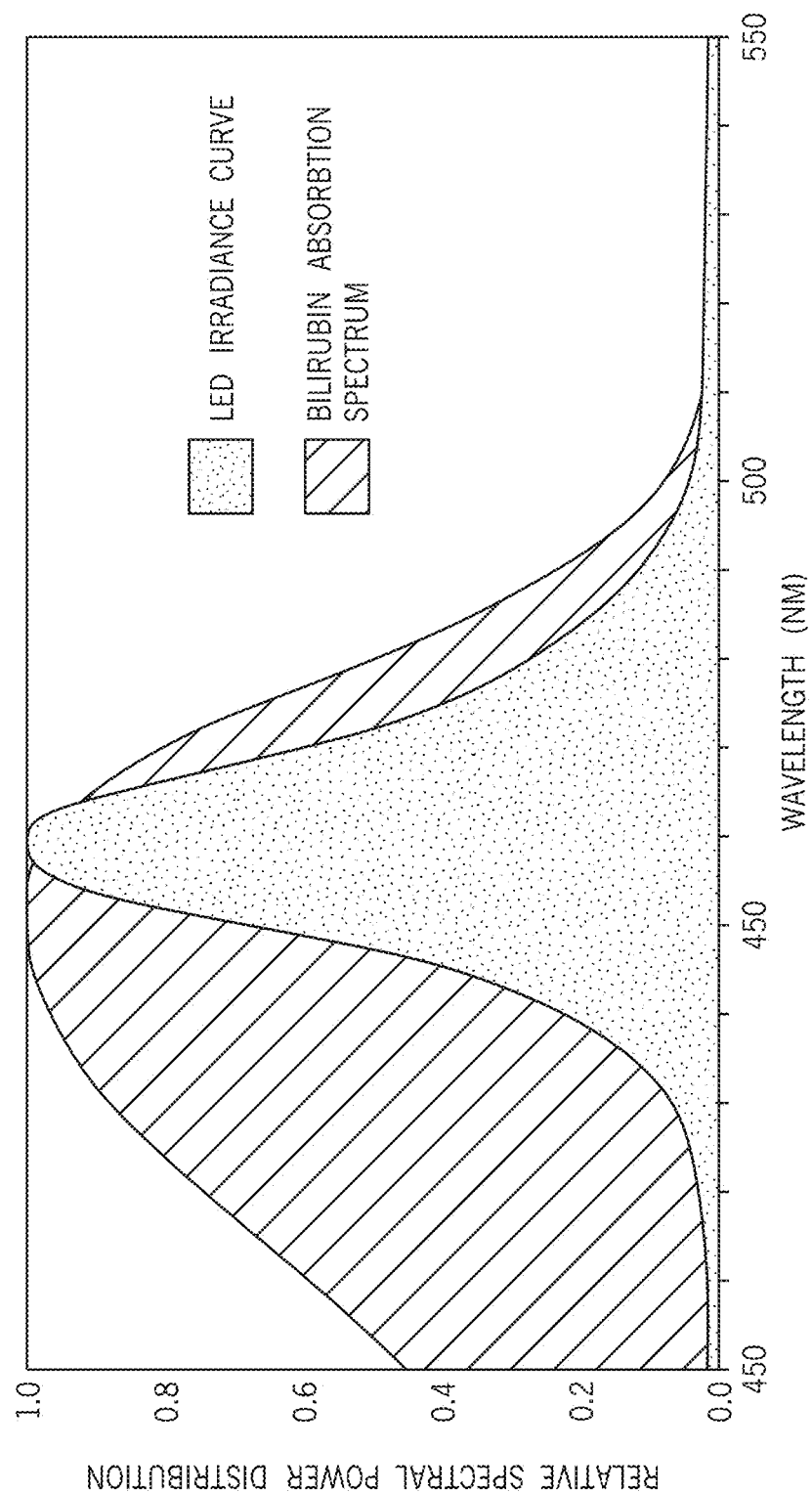
FIG. 16 is a graph illustrating a relative spectral power distribution as a function of wavelength for an LED of the phototherapy treatment apparatus of FIG. 3 and for bilirubin absorption according to one non-limiting example of the present disclosure.

FIG. 16 shows a portion of an absorption spectrum 500 for bilirubin as a function of wavelength and one non-limiting example of an output spectrum 502 for the plurality of LEDs 368. The output spectrum 502 shows in this non-limiting example that the light emitted from the plurality of LEDs 368 have a center wavelength of approximately 457 nm. In other non-limiting examples, the plurality of LEDs 368 may be configured to output light at a wavelength between approximately 350 nm to approximately 500 nm. It should be appreciated that the treatment of jaundice is but one non-limiting application of the phototherapy treatment apparatus 300 described herein, and the techniques and properties of the disclosed phototherapy treatment apparatus 300 may be applied to a number of phototherapy applications.

Figure 17:
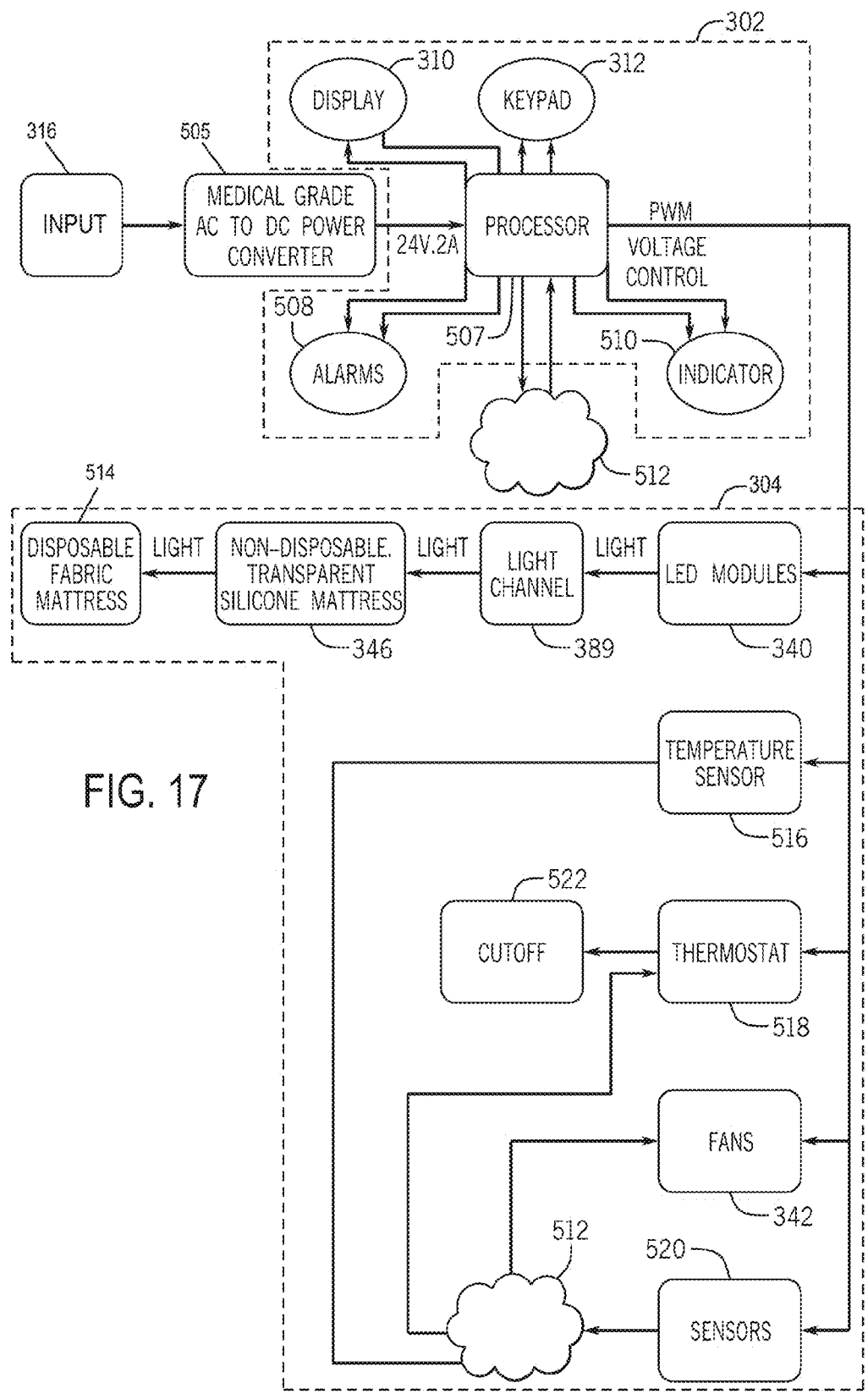
FIG. 17 a schematic illustration of the components of the phototherapy treatment apparatus of FIG. 3 according to one non-limiting example of the present disclosure.

FIG. 17 is a schematic diagram illustrating one non-limiting example of the phototherapy treatment apparatus 300. As shown, power can be supplied to the control unit 302 through the input 316 of the bed assembly 304, which can then be directed through a medical grade power converter 505 to the control unit 302. In one non-limiting example, the power supplied to the input 316 may be wall power (e.g., 120V AC power). In other non limiting examples, the input 316 may be configured to receive power from a portable power supply, such as a battery that can be rechargeable via solar energy.

A processor 507 of the control unit 302 is in communication with the display 310, the keypad 312, an alarm 508, an indicator 510, and a cloud 512. The processor 507 is also in communication with the bed assembly 304, via control unit 302 through the printed circuit board 354 of the bed assembly 304. The printed circuit board 354 can receive power relayed from the medical power converter 505 by the control unit 302 to power the LED modules 340 and, specifically, to the plurality of LEDs 368. The control unit 302 can be configured to control a voltage supplied to the plurality of LEDs 368 to control an intensity of the light emitted onto the incident surfaces 386, through the light channel 389 and the pad 346 and then to the patient (e.g., a neonate). In some non-limiting examples, the light emitted by the plurality of LEDs 368 may travel through a disposable fabric mattress 514, as discussed below.

The bed assembly 304 may include a temperature sensor 516 (e.g., a thermistor) in communication with the control unit 302 and configured to measure a temperature at one or more locations within the bed assembly 304. For example, the bed assembly 304 may include a temperature sensor 516 to measure a temperature of the plurality of LEDs 368 and/or at a location adjacent to the patient (e.g., a neonate) to prevent dehydration. The processor 507 can be configured to electrically shut down the phototherapy treatment apparatus 300 if the temperature sensor 516 measured a temperature within the bed assembly 304 that exceeds a predetermined temperature limit. The bed assembly 304 may further include a thermostat 518, and a plurality of sensors 520 each in communication with the control unit 302. The thermostat 518 may include a cutoff 522 configured to mechanically cutoff and shut down the phototherapy treatment apparatus 300 if a temperature within the bed assembly 304 exceeds a predetermined temperature limit. The plurality of sensors 520 may be configured to measure one or more of temperature, air flow, voltage, humidity and current. The control unit 302 is also in communication with the fans 342 and configured to selectively instruct the fans 342 to provide air flow throughout the air passageway 394 to aid in the heat dissipation provided by the heat sinks 350. Each of the temperature sensor 516, the thermostat 518, the fans 342, and the plurality of sensors 520 may also be in communication with the cloud 512 for remote control thereof.

Figure 18:
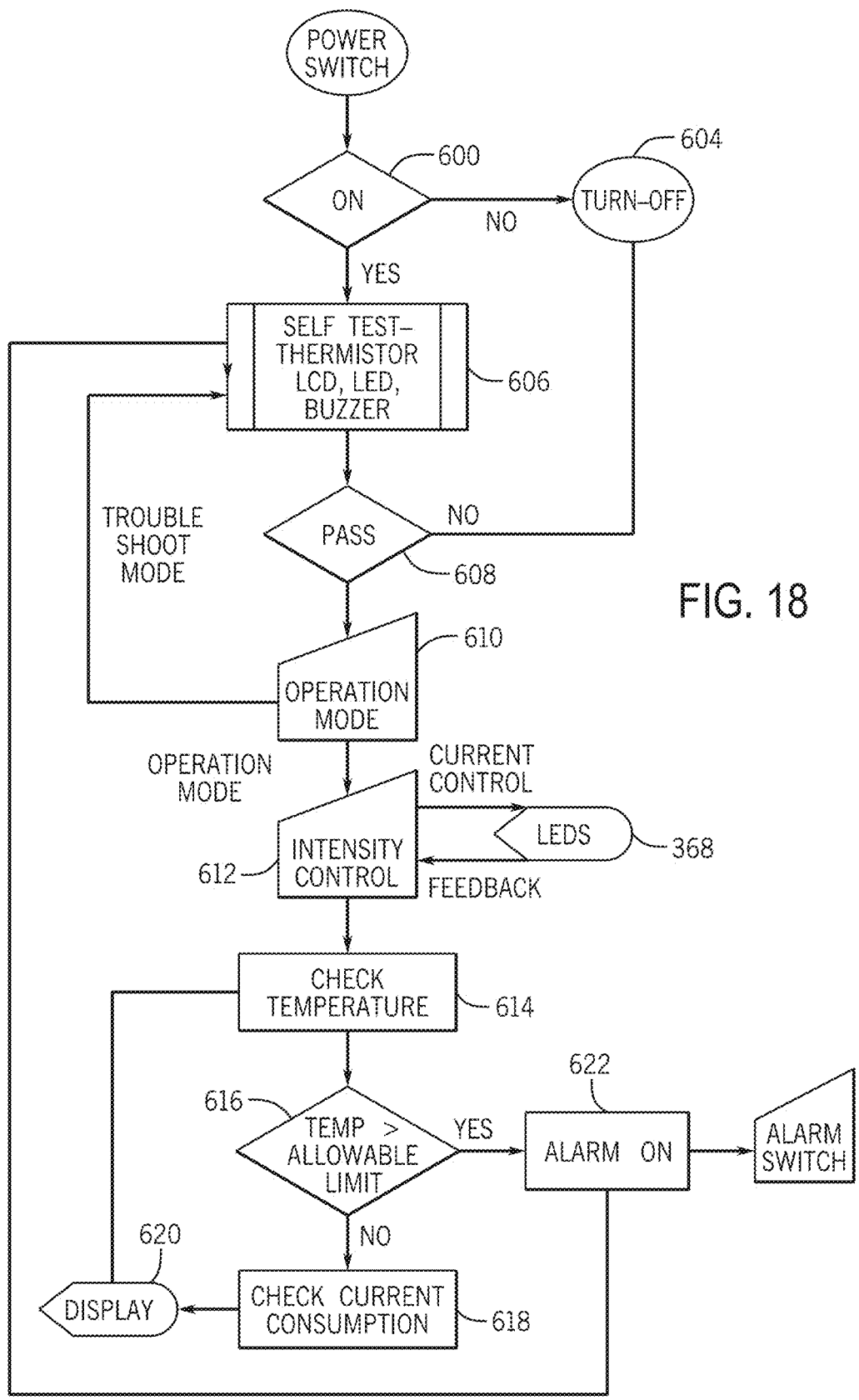
FIG. 18 is a flow chart outlining the steps for operating a phototherapy treatment apparatus according to one non-liming example of the present disclosure.

Referring now to FIG. 18, FIG. 18 is a flow chart illustrating one non-limiting example of how the phototherapy treatment apparatus 300 of the present disclosure may operate to treat a patient. At step 600, a determination is made as to whether a power switch is turned on. If the determination is that the power is not on, no power is supplied to the bed assembly 304 and the control unit 302, as illustrated at step 604. If the determination is that the power is on, a self test is performed at step 606. During the self test, control unit 302 determination is made at step 608 as to whether the components of the apparatus are functioning properly (e.g., the LED modules 340, the temperature sensor 516, the thermostat 518, the fans 342, and/or the sensors 520). If the components are not functioning properly, the apparatus can turn off the bed assembly 304. If the components are functioning properly, then the apparatus continues to an operation mode at step 610. In the operation mode of step 610, the apparatus controls an intensity of the light source, at step 612. For example, the control unit 302 of apparatus 300 may be configured to control a current and/or a voltage supplied to the plurality of LEDs 368 either automatically or in response to a users inputs to the keypad 312. The control unit 302 can receive feedback from the plurality of LEDs 368 to continuously monitor and adjust the output characteristics of the plurality of LEDs 368. When the control unit 302 provides power to the plurality of LEDs 368, the plurality of LEDs 368 emit treatment light onto the incident surfaces 386 at a viewing angle that ensures TIR along the light channel 389. The treatment light then totally internally reflects along the light channel 389 until they contact one or more of the plurality of microstructures 384 of the treatment surface 382. The plurality of microstructures 384 are configured to disperse the treatment light and diffusely emit the light from the treatment surface 382 to a patient laying on the top side 374. In the non-limiting example where the plurality of LEDs 368 can be configured to emit light capable of photodissociating bilirubin, the patient can be a jaundiced neonate and the light diffusely emitted from the treatment surface 382 can aid in treating the jaundiced neonate. In other non-limiting examples, the plurality of LEDs 368 may be configured to output light at another wavelength, or range of wavelengths, to treat a patient with an alternative ailment treatable via phototherapy. In some non-limiting examples, the irradiance ratio provided by the bed assembly 304 may be between approximately 0.4 and 0.9. In other non-limiting examples, the irradiance ratio provided by the bed assembly 304 may be greater than approximately 0.4.

While in the operation mode, the apparatus can also monitor a temperature (e.g., via temperature sensor 516 and the thermostat 518) of the patient and/or the plurality of LEDs 368, as illustrated at step 614. The apparatus can determine at step 616 if the temperature(s) measured by the temperature sensor 516 is greater than an allowable limit. If the sensed temperature is not greater than the limit, the apparatus can measure a current consumption of the plurality of LEDs 368 at step 618 and output the current consumption to the display 310 at step 620. If the sensed temperature is greater than the limit, the apparatus can be configured to trigger an alarm at step 622. The alarm can be audio, visual and/or tactile. After triggering an alarm at step 622, the apparatus can re-enter the self test at step 606.

Figure 19:
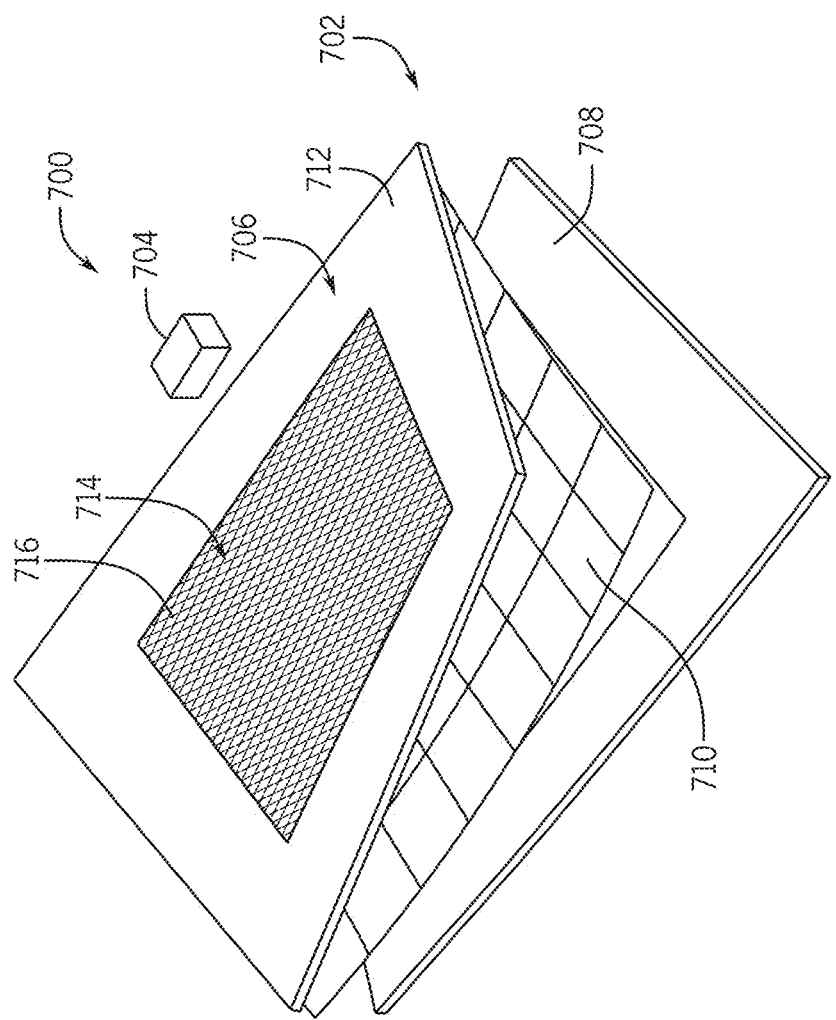
FIG. 19 is a perspective view of a phototherapy treatment apparatus including a heater according to another non-limiting example of the present disclosure.

FIG. 19 is a perspective view of another non-limiting example of a phototherapy treatment apparatus 700 of the present disclosure. Phototherapy treatment apparatus 700 includes a bed assembly 702 and a light source 704, which may or may not include a transition device (not shown). Bed assembly 702 includes an upper bed layer 706 and a lower bed layer 708, and a thin film 710 located or sandwiched between the layers 706, 708. The upper bed layer 706 includes a peripheral surface 712, which surrounds a treatment surface 714 containing a plurality of microstructures 716. The plurality of microstructures 716, which again can be voids, micro-cracks, chars, combinations therefore, or any other suitable microstructures capable of diffusing light. The microstructures 716 can likewise be formed by CNC machining, laser engraving, sand blasting, chemical engraving, combinations thereof, or other suitable mechanical, chemical, or photic operations. The properties of the microstructures 716 can be similar to the plurality of microstructures 384, described above. The light source 704 emits light that is transmitted into a light channel (not shown) formed by the bed assembly 702 between the top side 718 of the upper bed layer 706 and the bottom side 720 of the lower bed layer 708, such that TIR is achieved. The light is dispersed by the microstructures 716 to provide a diffuse intensity profile along the treatment surface 714. The thin film 710 can be a heat source that is transparent to the light emitted by the light source 704, allowing the phototherapy treatment apparatus 700 to control temperature of the treatment surface 714, while providing an evenly diffused amount of light to a patient during treatment. By controlling the temperature of the treatment surface 714, in this non-limiting example, the phototherapy treatment apparatus 700 could be used to treat both a phototherapy treatable ailment (e.g., jaundice, eczema, atopic dermatitis, vitiligo, psoriasis, seasonal affective disorder, bipolar disorder, wound healing, and inhibiting bacterial growth) and hypothermia. Heat source 714 in one example includes a resistive heater and at least one of a transparent or translucent material. In another non-limiting example, the heat source 714 can be configured to provide heating via another heating mechanism (e.g., chemical, mechanical, conduction, convection, and/or radiation).

Figure 20:
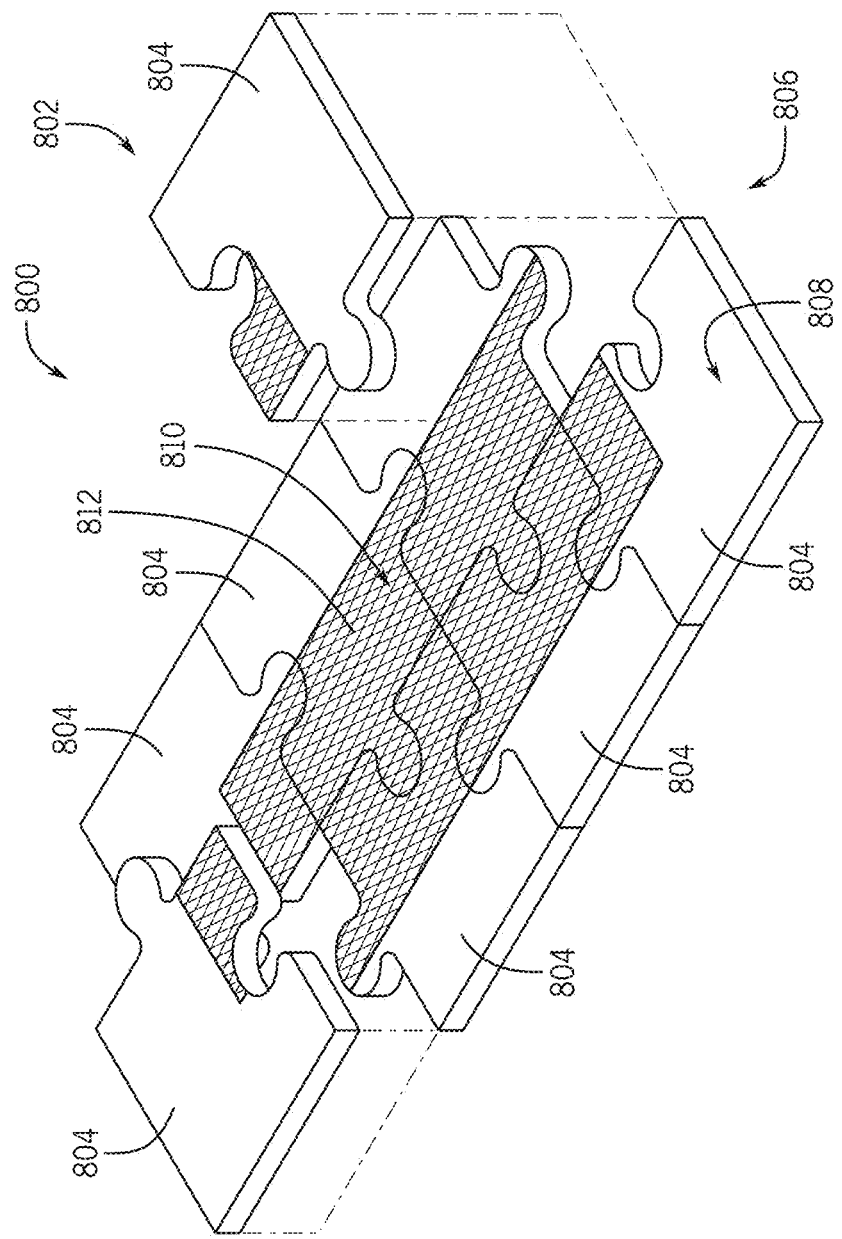
FIG. 20 is a perspective view of a phototherapy treatment apparatus configured for piecewise assembly according to another non-limiting example of the present disclosure.
Figure 21:
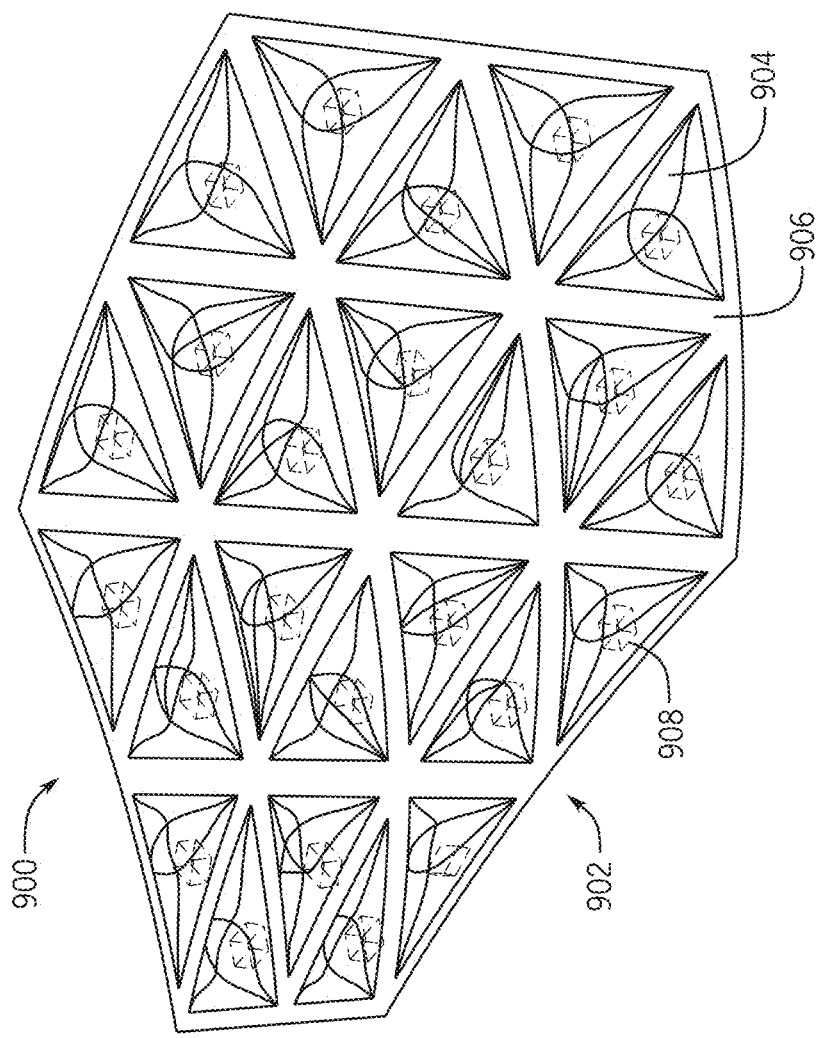
FIG. 21 is a perspective view of a phototherapy treatment apparatus including a plurality of foldable unit cells according to another non-limiting example of the present disclosure.

FIGS. 20 and 21 illustrate two additional non-limiting examples of phototherapy treatment apparatuses of the present disclosure. The apparatuses of FIGS. 20 and 21 are constructed to include a plurality of unit cells that enhance portability. For example, FIG. 20 is a perspective view of a phototherapy treatment apparatus 800 in which a bed assembly 802 is separated into a plurality of unit cells constructed as modular pieces 804, which assemble to form a bed 806, with a peripheral surface 808 and a treatment surface 810 containing a plurality of microstructures 812. The properties of the plurality of microstructures 812 can be similar to the plurality of microstructures 384, described above. The puzzle-like shape of the plurality of modular pieces or unit cells 804 is meant to show one possible method for coupling the plurality of modular pieces 804 together, and is not meant to be limiting. In other non-limiting examples, the modular pieces 804 can be coupled through a variety of mechanical and chemical methods including joints, hinges, adhesives or any other suitable coupling method. The phototherapy treatment apparatus 800 may also include a frame (not shown) capable of containing the plurality of modular pieces 804, such that the plurality of modular pieces 804 can be arranged within the frame and held in place without direct coupling therebetween. The plurality of modular pieces 804 increase the portability of the apparatus. Again, the plurality of microstructures 812 in this non-limiting example can be voids, micro-cracks, chars, combinations thereof, or any other suitable microstructures capable of diffusing light, and can be formed by CNC machining, laser engraving, sand blasting, chemical engraving, combinations thereof, or any other suitable mechanical, chemical, or photic operations.

FIG. 21 is a perspective view of a phototherapy treatment apparatus 900 of the present disclosure in which the plurality of unit cells 904 are connected by a flexible filler material 906, such that a bed assembly 902 can be folded into a smaller configuration to improve portability. Bed assembly 902 can have a plurality of light sources 908 placed directly below the plurality of unit cells 904, or can have a single light source 908 placed along an edge of the bed assembly 902 such that the structure of the bed assembly 902 can be completely collapsible. One non-limiting example of a method for collapsing the bed assembly 902 would be to form the plurality of unit cells 904 and the flexible filler material 906 such that the bed assembly 902 is capable of utilizing Origami folding patterns, such as Miura Ori and Ron Resch, to provide effective collapsibility, thereby allowing for increased portability.

Figure 22:
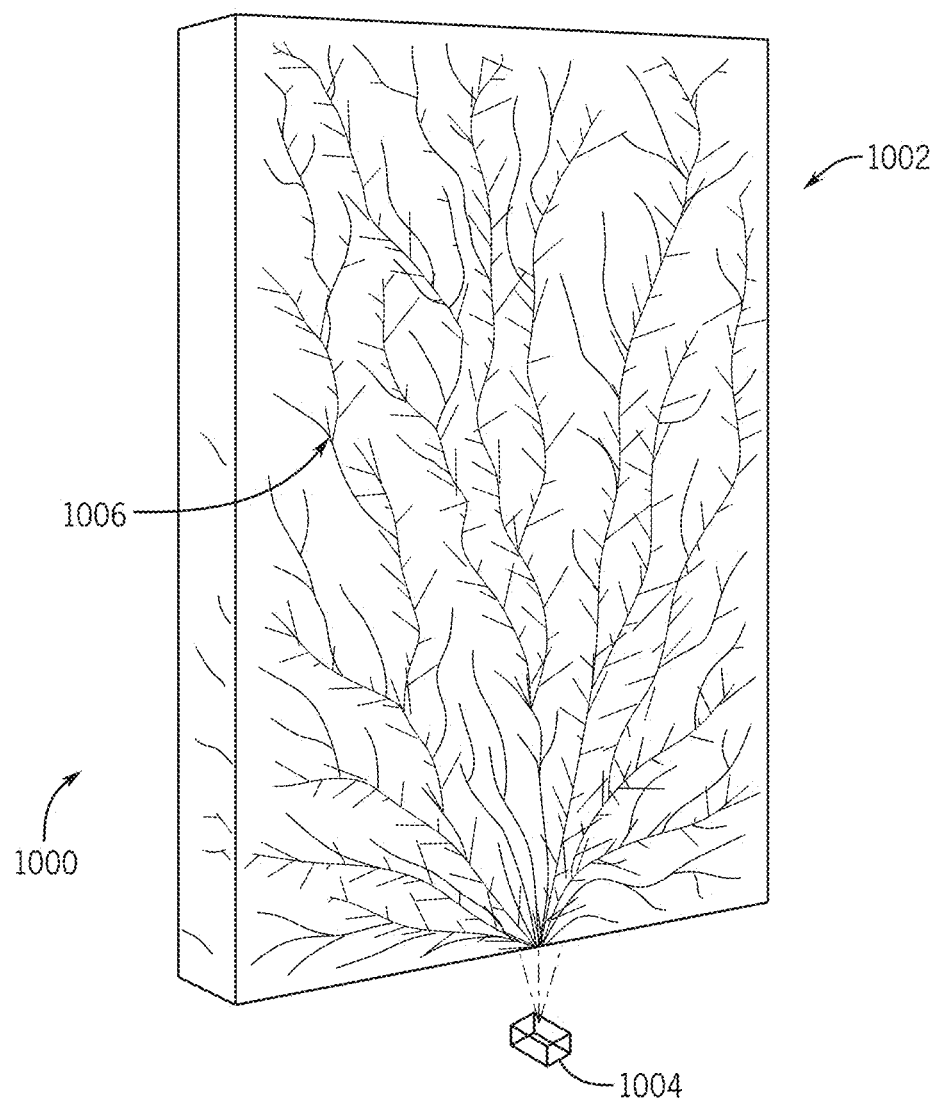
FIG. 22 is a perspective view of a phototherapy treatment apparatus including a branched structure for light transmission according to another non-limiting example of the present disclosure.

FIG. 22 is a perspective view of yet another non-limiting example of a phototherapy treatment apparatus 1000 of the present disclosure. In this non-limiting example, the phototherapy treatment apparatus 1000 includes a bed 1002 and a light source 1004. The bed 1002 contains a plurality of dendrites 1006 or branched tree channels, which form a Litchenberg figure within the bed 1002. The Litchenberg figure is produced by focusing high voltage at a single point on a surface of the bed 1002. When a closed path is provided, electrons effectively eat through the material to produce the dendrites 1006. Similar to the light channels in the previous examples, the dendrites 1006 are capable of efficiently carrying light from the light source 1004 to a treatment surface (not shown), which again would contain a plurality of microstructures (not shown) that would be capable of dispersing light emitted by the light source 1004 to provide a diffuse light intensity along the treatment surface (not shown).

Figure 23:
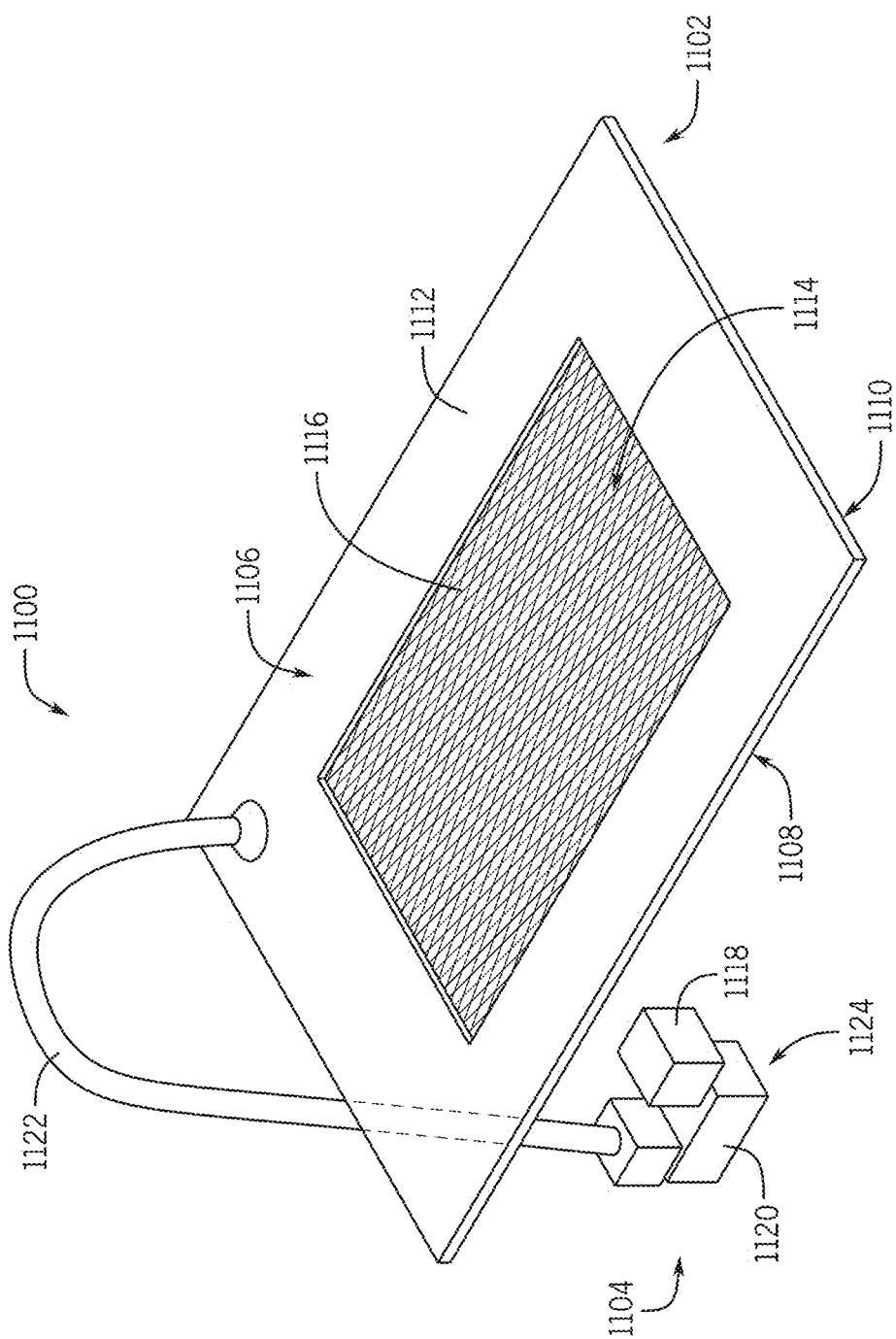
FIG. 23 is a perspective view of a phototherapy treatment apparatus including a goose necked light source according to another non-limiting example of the present disclosure.

FIG. 23 is a perspective view of yet another non-limiting example of a phototherapy treatment apparatus 1100 of the present disclosure. In this non-limiting example, the phototherapy treatment apparatus 1100 includes a bed 1102 and a light apparatus 1104. The bed 1102 has a top surface 1106, a bottom surface 1108, and a plurality of side surfaces 1110. The top surface 1106 includes a peripheral surface 1112 and a treatment surface 1114, which includes a plurality of microstructures 1116. The properties of the plurality of microstructures 1116 can be similar to the plurality of microstructures 384, described above. The light apparatus 1104 includes a light source 1118 including a transition device (not shown), a heat sink 1020, and a gooseneck light 1122, all coupled to a circuit board 1124. The gooseneck light 1122 can be used in conjunction with the light source 1018 if the light emitted through the treatment surface 1114 is insufficient. Alternatively or additionally, the gooseneck light 1122 can be configured to output infrared heat to the patient.

Figure 24:
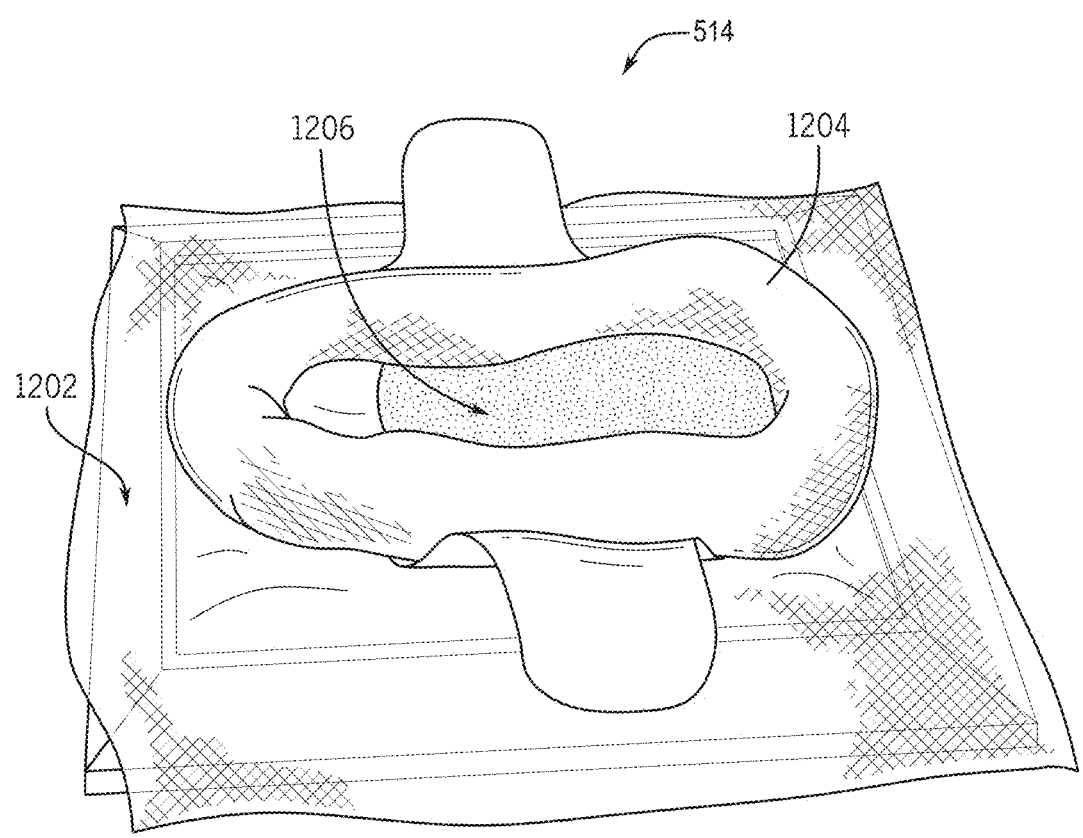
FIG. 24 is a perspective view of a disposable mattress usable with phototherapy treatment apparatuses described herein.

FIG. 24 is a perspective view of a non-limiting example of an optional disposable fabric mattress 514, which can be used in conjunction with any of the phototherapy treatment apparatuses of the present disclosure. The mattress 514 provides a comfortable surface for a neonate during treatment and confines the neonate within the treatment surface. The mattress 514 includes a porous fabric sheet 1202, a foam liner 1204, and a gel pad 1206. The porous fabric sheet 1202 is at least one of transparent or translucent, antimicrobial, and waterproof. The foam liner 1204 can house beads (not shown), which can aid in the diffusion of light. A gel pad 1206 is configured to support the head of a patient (e.g., a neonate) during treatment.

It should be appreciated that the techniques and properties of the phototherapy treatment apparatuses described herein may be applied to other phototherapy applications other than treating a jaundiced neonate.

EXAMPLES

The following examples set forth, in detail, was that the phototherapy treatment apparatuses described herein may be used or implemented, and will enable one of skill in the art to more readily understand the principals thereof. The following examples are presented by way of illustration and are not meant to be limiting in any way.

Three samples were prepared to simulate a treatment surface including the plurality of microstructures described herein. The three were fabricated from PMMA and were treated using three different kinds of processes—sandblasting, laser etching, and CNC machining. In particular, a first PMMA sample was CNC treated and laser etched, a second PMMA sample was CNC treated and sandblasted, and a third PMMA sample was only CNC treated. The three samples were placed under an optical profilometer (Zygo ZeScope) to capture the surface of the samples in three-dimensions (3D). Images acquired by the profilometer produced two sets of data—point cloud data and image profiles. The point cloud data was post processed to reconstruct the 3D surfaces and to calculate the roughness of the surfaces.

Figure 25:
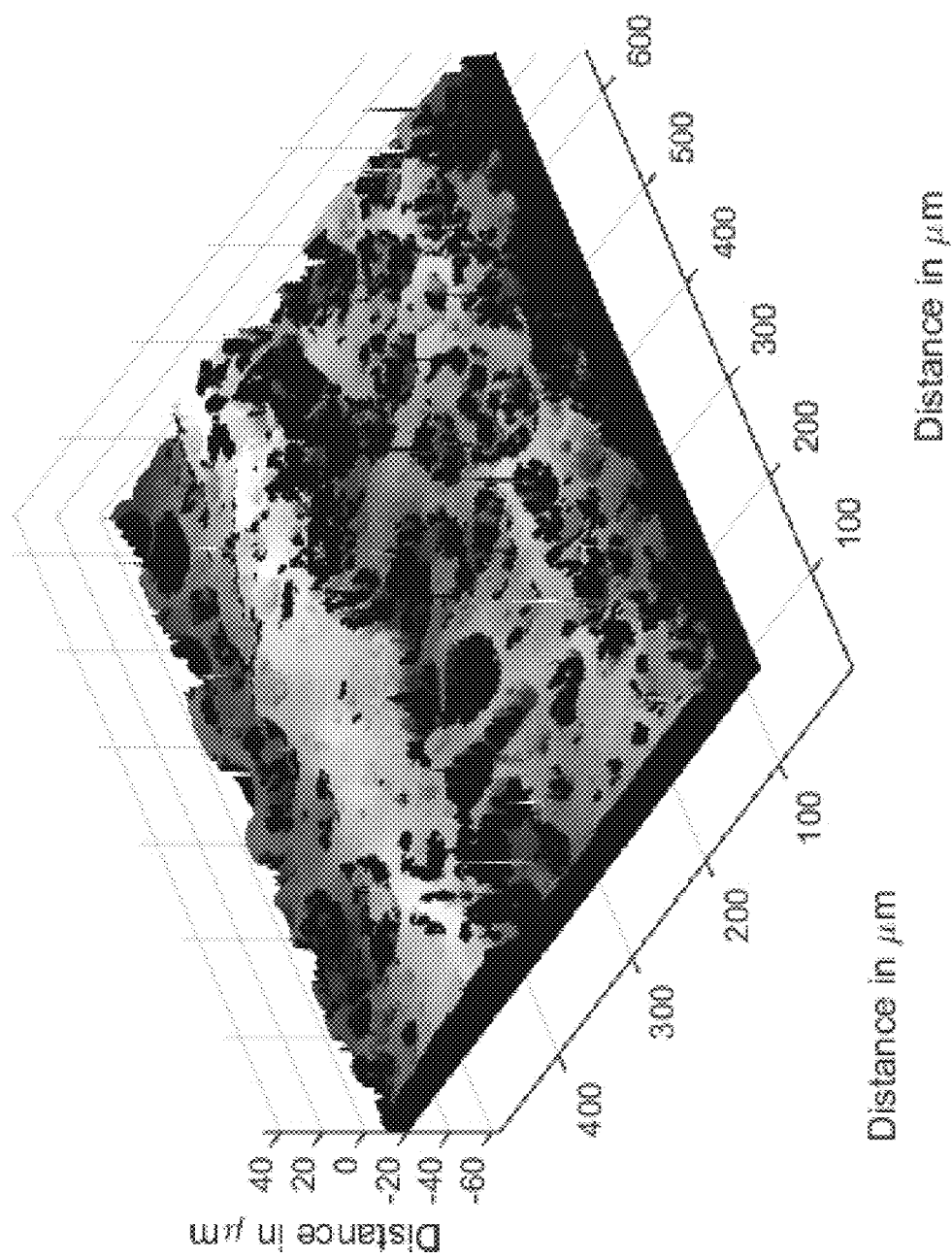
FIG. 25 is a perspective view of a surface profile of a bed surface treated by CNC.
Figure 26:
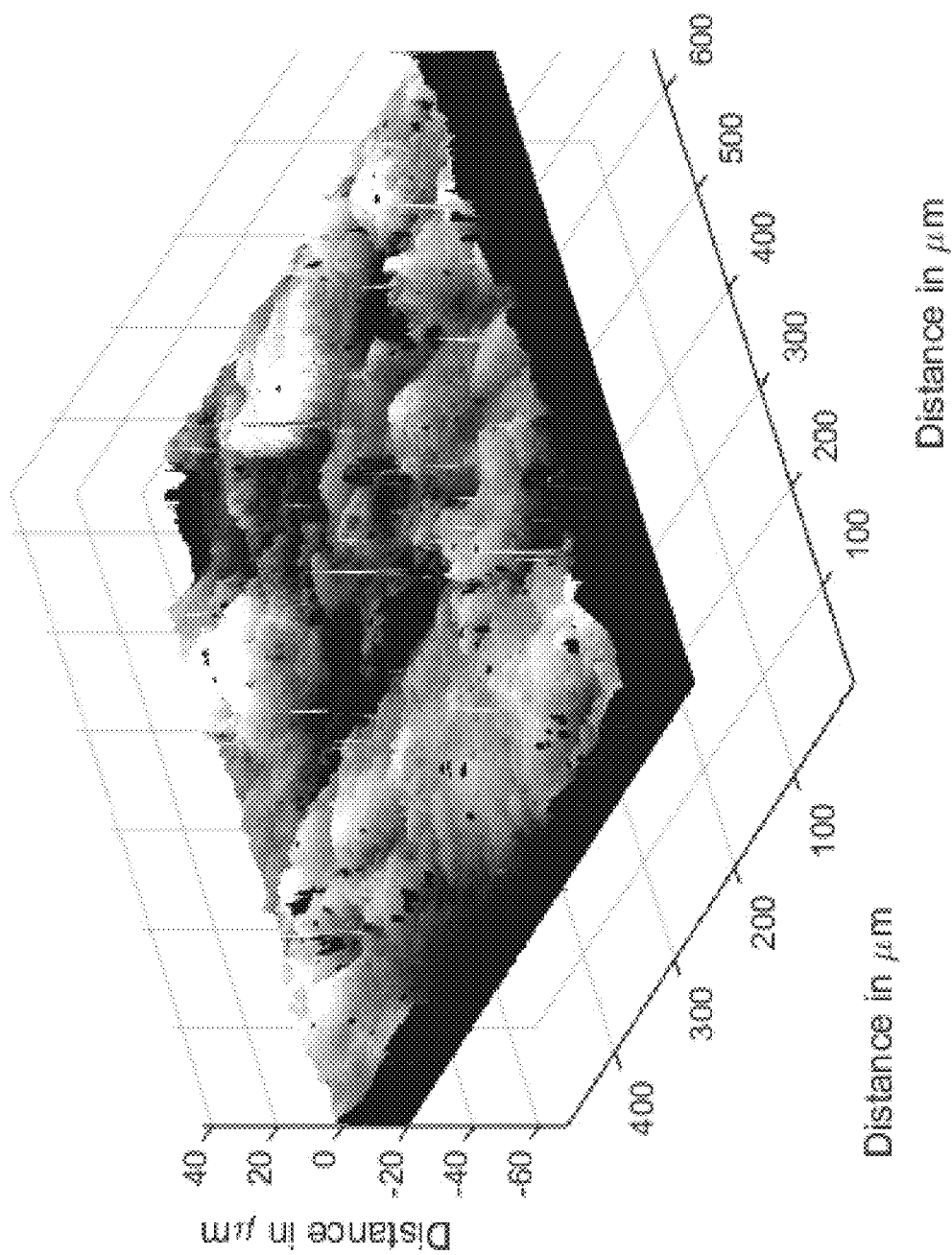
FIG. 26 a perspective view of a surface profile of a bed surface treated by CNC and laser etching.
Figure 27:
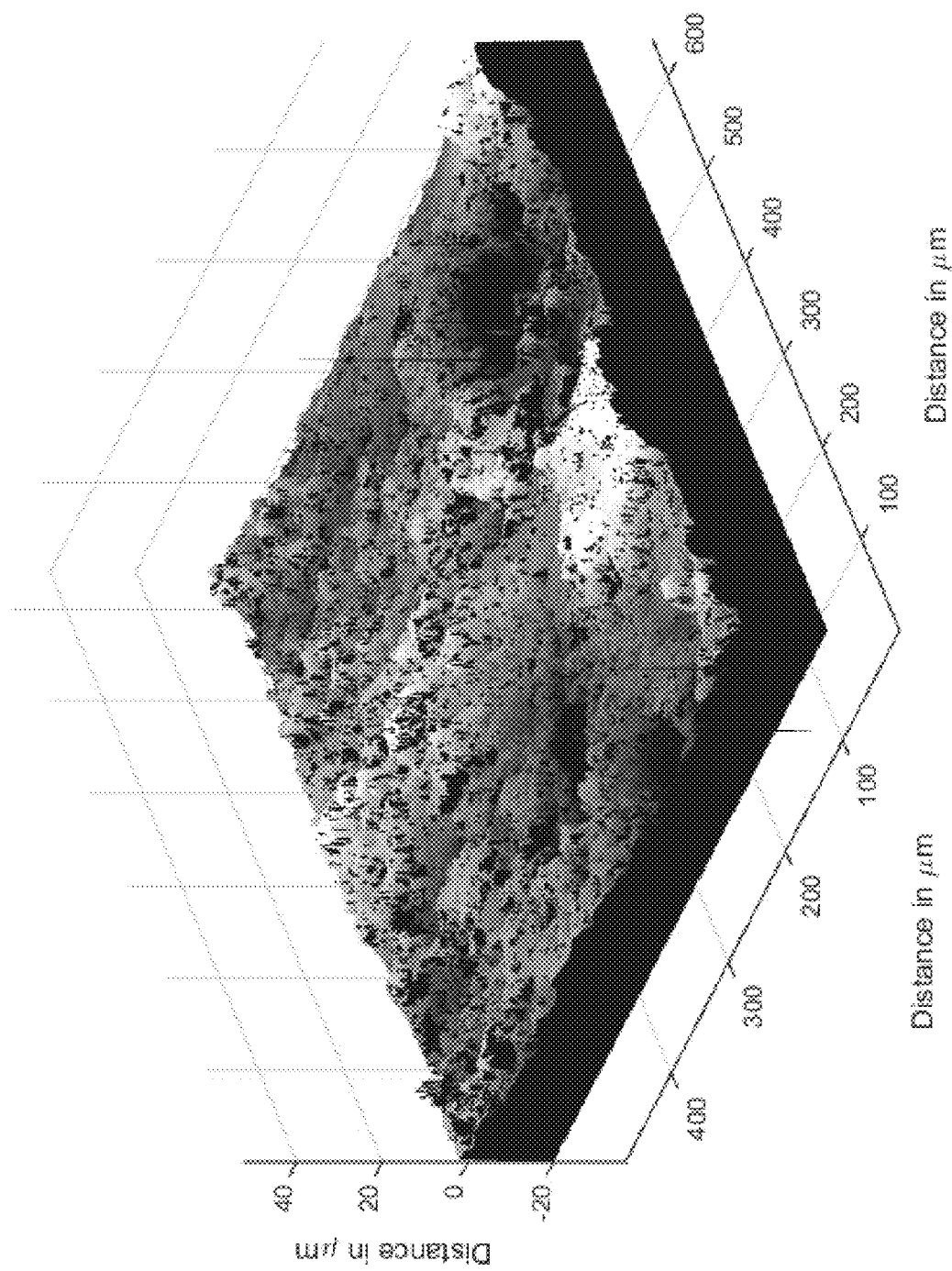
FIG. 27 is a perspective view of a surface profile of a bed surface treated by CNC and sandblasting.

FIGS. 25-27 show the surface profiles for the three PMMA samples. Specifically, FIG. 25 shows the surface profile of the first sample that was CNC treated and laser etched, FIG. 26 shows the surface profile of the second sample that was CNC treated and sandblasted, and FIG. 27 shows the surface profile of the sample that was only CNC treated. As shown in FIGS. 25 and 26, for the laser etched (FIG. 25) and sandblasted (FIG. 26) samples, the surface appears indented, which compliments the shape and size of the projectiles in the respective process. There are not many sharp changes in topography, except for dislocations and chipping. The voids formed by the projectiles appear to be clearer due to the fact that there is a considerably high localized temperature rise at the point of contact. Based on FIGS. 25 and 26—which show only minor fluctuations in topography—the directions change of gradient surface normals is more gradual with in a small area, results in a more uniform light intensity profile.

As shown in FIG. 27, for the CNC treated sample, there are small fissures running deep into the surface and can play a major role in trapping light inside the medium. The directions of the surface normals change rapidly within a small neighborhood. In this non-limiting example, the voids formed can be so small they can be considered as cracks.

The results of FIGS. 25-27 suggest that only CNC treating a surface (without laser etching or sandblasting) can result in a surface with a higher roughness, which may result in a higher light emittance but a less uniform distribution. To confirm this, the average roughness and average absolute slopes were calculated for each of the three samples tested. The average roughness can be defined as the area between the roughness profile and its mean line, or as the integral of the absolute value of the roughness profile height over the evaluation length. The average roughness, $R_a$, can be defined as:

$$R_a = \frac{1}{L}\int_0^L |r(x)|dx \qquad (6)$$

or as:

$$R_a = \frac{1}{L}\sum_1^n |r_n|. \qquad (7)$$

Another parameter than can be used to characterize a surfaces roughness is the average absolute slope. The average absolute slope can be defined as the average absolute value of the slope of the roughness profile over the evaluation length. The average absolute slope, $\Delta_a$, can be defined as:

$$\Delta_a = \frac{1}{L}\int_0^L \left|\frac{dr(x)}{dx}\right|dx \qquad (8)$$

or as:

$$\Delta_a = \frac{1}{L}\sum_{n-1}^n |r_{n+1} - r_n|. \qquad (9)$$

The average roughness $R_a$ and the average absolute slope $\Delta_a$ can be used to represent the roughness of a surface. It should be appreciated that the average roughness $R_a$ alone may not be sufficient determine if one surface is rougher than another. Surfaces with similar profiles can have similar Ra values. Thus, the average absolute slope parameter is also considered. Table 1 below shows the average roughness $R_a$ and average absolute slope $\Delta_a$ values for the three samples of FIGS. 25-27.

TABLE 1

| Sample | Operation | $R_a$ (µm) | $\Delta_a$ (no units) |
| --- | --- | --- | --- |
| FIG. 25 | CNC + LASER | 2.4621 | 3.44 |
| FIG. 26 | CNC + SANDBLAST | 2.7286 | 1.32 |
| FIG. 27 | CNC | 1.6445 | 5.82 |

As shown in Table 1, the samples that were CNC treated and laser etched, and CNC treated and sandblasted had a higher average roughness, but the surface that was only CNC treated showed a significantly higher average absolute slope. The light intensity output from the treatment surface 382 can be correlated with the surface roughness, which can be described using $R_a$ and $\Delta_a$. Based on the results of Table 1, it would be expected that the sample that was only CNC treated would have a higher output light intensity when compared to the other samples. This hypothesis was tested by measuring a light output intensity profile as a function of position along the treated surfaces in each of the three samples of FIGS. 25-27.

Figure 28:
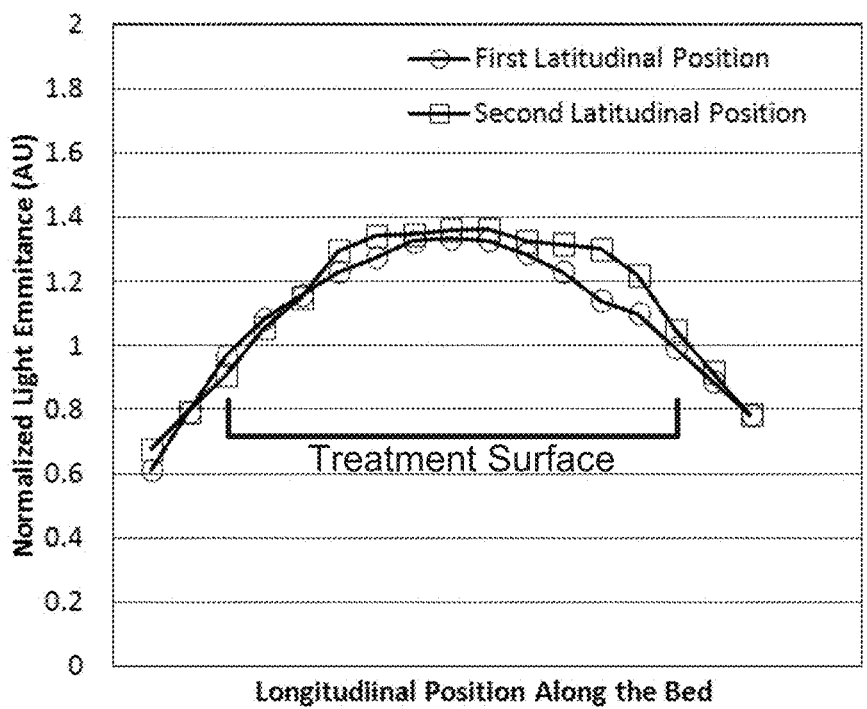
FIG. 28 is graph illustrating a normalized light emmitance as a function of longitudinal position along the bed surface of FIG. 25 at two different latitudinal positions.
Figure 29:
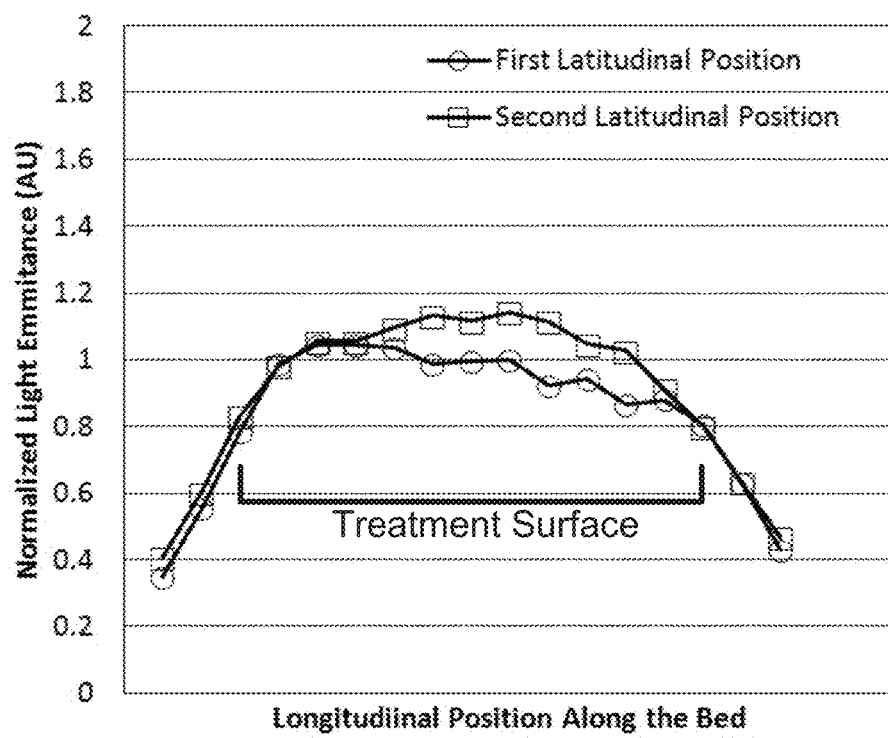
FIG. 29 is graph illustrating a normalized light emmitance as a function of longitudinal position along the bed surface of FIG. 26 at two different latitudinal positions
Figure 30:
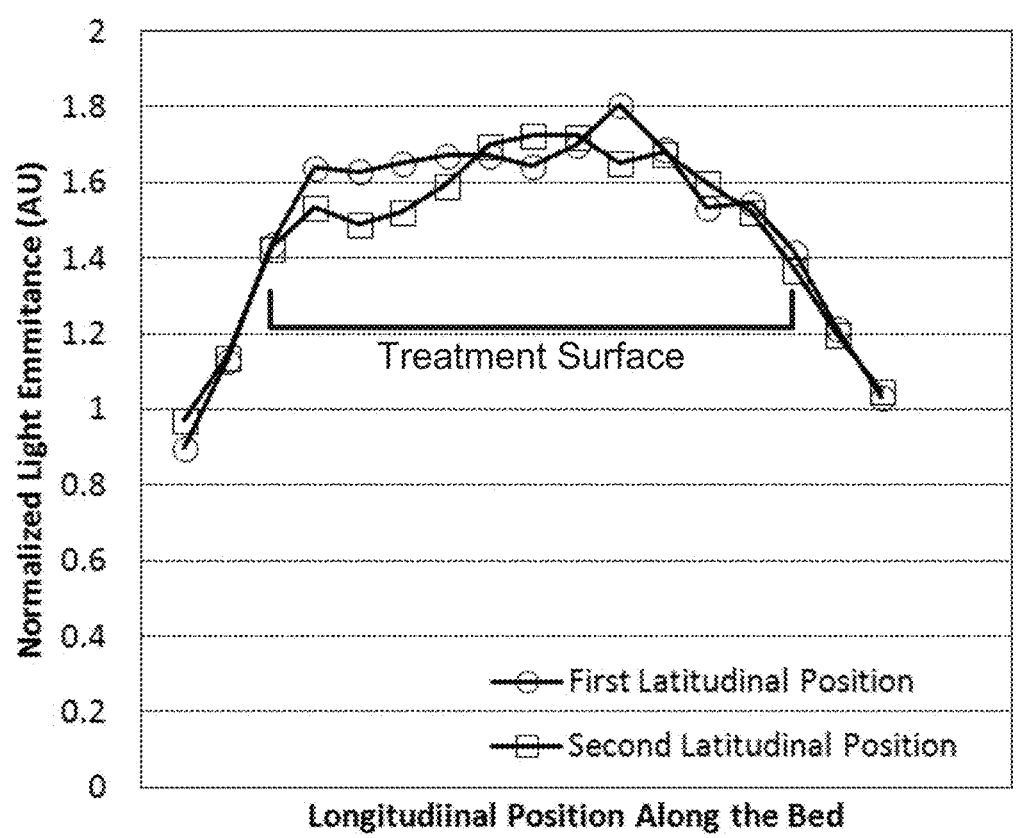
FIG. 30 is graph illustrating a normalized light emmitance as a function of longitudinal position along the bed surface of FIG. 27 at two different latitudinal positions

FIGS. 28-30 illustrate cross-sectional light profiles as a function of longitudinal position along the samples taken at two different latitudinal positions (one on each side of a center longitudinal axis of the sample). The graph of FIG. 28 corresponds with the measured light profile of the sample of FIG. 25, the graph of FIG. 29 corresponds with the measured light profile of the sample of FIG. 26, and the graph of FIG. 30 corresponds with the measured light profile of the sample of FIG. 30. The light emmitance values of FIGS. 28-30 are all normalized by an arbitrary value. As shown in FIGS. 28-30, the sample that was only CNC treated (FIGS. 27 and 30) indeed output a higher intensity of light than the samples that were laser etched (FIGS. 25 and 28) and sandblasted (FIGS. 26 and 29). In all cases, the light profile output by the samples achieved a irradiance ratio greater than 0.4 over a treatment surface. Thus, the above-described treatment processes (e.g., CNC, laser etching, and sandblasting) can be used to form a plurality of microstructures in the treatment surface and disperse light such that a diffuse light profile is output to a patient.

The examples described herein suggest that, in order to achieve the desired light output characteristics (i.e., diffuse profile and an irradiance ratio >0.4), that the average roughness $R_a$ can be between approximately 1 µm and approximately 20 µm, and the average absolute slope can be between approximately 2 and approximately 15. It should be appreciated that the properties and techniques of the plurality of microstructures described herein may be achieved using alternative manufacturing processes. Also, it should be appreciated that the use of the plurality of microstructures to achieve the desired optical output characteristics may be applied to various phototherapy treatment apparatuses and methods.

Thus, while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A phototherapy treatment method comprising:
    placing a patient on a top surface of a bed having at least one of a translucent or transparent material; generating light from a light source;
    directing the generated light at one of a plurality of side surfaces of the bed so that the generated light transmits through the material of the bed to produce total internal reflection of the generated light; and
    transmitting the generated light through a plurality of microstructures located on the top surface of the bed such that the light exits the plurality of microstructures having a more diffusive distribution so as to enhance the treatment of an ailment of the patient placed on the bed.

2. The phototherapy treatment method of claim 1, which includes transmitting the light generated by the light source through a transition device structured to at least one of (i) focus, (ii) scatter or (iii) diffuse the light rays.

3. The phototherapy treatment method of claim 1, wherein the plurality of microstructures are arranged on the top surface of the bed.

4. The phototherapy treatment method of claim 1, further comprising:
    placing the light source in contact with a heat sink to dissipate heat generated by the light source.

5. The phototherapy treatment method of claim 1, wherein the plurality of microstructures include at least one of voids, cracks, or char particles.

6. The phototherapy treatment method of claim 5, further comprising:
    forming the plurality of microstructures via one or more of CNC machining, laser engraving, sand blasting, and chemical engraving.

7. The phototherapy treatment method of claim 1, wherein the plurality of microstructure include greater than approximately 1000 cracks per square inch.

8. The phototherapy treatment method of claim 1, wherein the top surface of the bed defines inwardly sloped channel to intersect the light transmitted from the one of the plurality of side surfaces and through the material of the bed, and wherein the inwardly sloped channel is configured to concentrate the light that exits the plurality of microstructures and increase an area of the patient exposed to the light.

9. The phototherapy treatment method of claim 1, further comprising:
    covering the surface of the bed with a cover pad having at least one of a transparent or translucent material, the cover pad being sealingly engages to the surface of the bed to prevent liquid from contacting the light source and to provide a cushion to the patient.

10. The phototherapy treatment method of claim 1, wherein the light source is configured to generate light having a wavelength between approximately 350 nanometers and 550 nanometers.

* * * * *

UNITED STATES PATENT AND TRADEMARK OFFICE
CERTIFICATE OF CORRECTION

PATENT NO. : 10,369,376 B2
APPLICATION NO. : 15/143277
DATED : August 6, 2019
INVENTOR(S) : Sivakumar Palaniswamy et al.

Page 1 of 1

It is certified that error appears in the above-identified patent and that said Letters Patent is hereby corrected as shown below:

In the Specification

Column 5, Line 45, "SAID" should be --SAD--.

Signed and Sealed this
Twenty-fourth Day of September, 2019

Andrei Iancu
*Director of the United States Patent and Trademark Office*